(12) United States Patent
McGuckin, Jr. et al.

(10) Patent No.: US 9,675,474 B2
(45) Date of Patent: *Jun. 13, 2017

(54) VASCULAR DEVICE WITH VALVE FOR APPROXIMATING VESSEL WALL

(71) Applicant: Rex Medical, L.P., Conshohocken, PA (US)

(72) Inventors: James F. McGuckin, Jr., Radnor, PA (US); Peter W. J. Hinchliffe, Campbell Hall, NY (US)

(73) Assignee: Rex Medical, L.P., Conshohocken, PA (US)

( * ) Notice: Subject to any disclaimer, the term of this patent is extended or adjusted under 35 U.S.C. 154(b) by 38 days.

This patent is subject to a terminal disclaimer.

(21) Appl. No.: 14/176,126

(22) Filed: Feb. 9, 2014

(65) Prior Publication Data

US 2014/0155988 A1    Jun. 5, 2014

Related U.S. Application Data

(60) Continuation of application No. 12/880,499, filed on Sep. 13, 2010, now Pat. No. 8,668,730, which is a
(Continued)

(51) Int. Cl.
*A61F 2/06* (2013.01)
*A61F 2/82* (2013.01)
(Continued)

(52) U.S. Cl.
CPC .......... *A61F 2/82* (2013.01); *A61B 17/12036* (2013.01); *A61B 17/12109* (2013.01);
(Continued)

(58) Field of Classification Search
CPC .... A61F 2/958; A61F 2002/9505; A61F 2/07; A61F 2/856; A61F 2250/0039; A61F 2/954; A61F 2/86
See application file for complete search history.

(56) References Cited

U.S. PATENT DOCUMENTS

| 4,275,469 A | 6/1981 | Gabbay |
| 4,759,758 A | 7/1988 | Gabbay |

(Continued)

FOREIGN PATENT DOCUMENTS

| DE | 19857887 | 7/2000 |
| EP | 1894543 | 3/2008 |

(Continued)

OTHER PUBLICATIONS

European Search Report dated Aug. 8, 2013 for European Patent Application No. 13164268.8.

*Primary Examiner* — Ann Schillinger
(74) *Attorney, Agent, or Firm* — Neil D. Gershon

(57) ABSTRACT

A vascular device comprising a plurality of vessel engaging members and a valve. The device is movable from a collapsed insertion position having a first diameter to a second expanded position having a second diameter larger than the first diameter. The plurality of vessel engaging members extend outwardly from the device for securely engaging the internal wall of a vessel upon expansion of the device to the second expanded position, wherein the vessel engaging members pull the internal wall of the vessel radially inwardly upon movement of the device from the second expanded position toward a first expanded position having a third diameter greater than the first diameter and less than the second diameter. In the first expanded position the valve is movable between an open position to allow blood flow therethrough to a closed position to prevent blood flow.

11 Claims, 35 Drawing Sheets

Related U.S. Application Data continuation of application No. 10/706,685, filed on Nov. 12, 2003, now Pat. No. 7,833,262, which is a division of application No. 10/011,345, filed on Dec. 5, 2001, now Pat. No. 6,676,698, and a continuation-in-part of application No. 09/877,639, filed on Jun. 8, 2001, now Pat. No. 6,695,878, and a continuation-in-part of application No. 09/877,480, filed on Jun. 8, 2001, now Pat. No. 6,527,800.

(60) Provisional application No. 60/317,801, filed on Sep. 7, 2001, provisional application No. 60/214,120, filed on Jun. 26, 2000.

(51) Int. Cl.
- A61B 17/064 (2006.01)
- A61B 17/12 (2006.01)
- A61B 17/00 (2006.01)
- A61F 2/24 (2006.01)
- A61F 2/848 (2013.01)

(52) U.S. Cl.
CPC ...... *A61B 17/12172* (2013.01); *A61F 2/2445* (2013.01); *A61F 2/2475* (2013.01); *A61B 17/0644* (2013.01); *A61B 17/12022* (2013.01); *A61B 2017/00867* (2013.01); *A61B 2017/0641* (2013.01); *A61F 2/2412* (2013.01); *A61F 2/2433* (2013.01); *A61F 2/2442* (2013.01); *A61F 2002/8483* (2013.01); *A61F 2210/0019* (2013.01); *A61F 2220/0016* (2013.01)

(56) References Cited

U.S. PATENT DOCUMENTS

| | | |
|---|---|---|
| 5,019,102 A | 5/1991 | Hoene |
| 5,147,389 A | 9/1992 | Lane |
| 5,151,105 A | 9/1992 | Kwan-Gett |
| 5,258,022 A | 11/1993 | Davidson |
| 5,350,398 A | 9/1994 | Pavenik et al. |
| 5,358,518 A | 10/1994 | Camilli |
| 5,375,612 A | 12/1994 | Cottenceau et al. |
| 5,395,390 A | 3/1995 | Simon et al. |
| 5,397,351 A | 3/1995 | Pavenik et al. |
| 5,397,355 A | 3/1995 | Marin |
| 5,411,552 A | 5/1995 | Anderson |
| 5,443,500 A | 8/1995 | Sigwart |
| 5,500,014 A | 3/1996 | Quijano et al. |
| 5,540,712 A | 7/1996 | Kleshinski et al. |
| 5,545,210 A | 8/1996 | Hess et al. |
| 5,562,728 A | 10/1996 | Lazarus |
| 5,591,197 A | 1/1997 | Orth |
| 5,593,417 A | 1/1997 | Rhodes |
| 5,609,598 A | 3/1997 | Laufer |
| 5,643,278 A | 7/1997 | Wijay |
| 5,674,279 A | 10/1997 | Wright |
| 5,746,766 A | 5/1998 | Edoga |
| 5,792,155 A | 8/1998 | Van Cleef |
| 5,800,526 A | 9/1998 | Anderson et al. |
| 5,810,847 A | 9/1998 | Laufer et al. |
| 5,827,322 A | 10/1998 | Williams |
| 5,843,164 A | 12/1998 | Frantzen et al. |
| 5,855,601 A | 1/1999 | Bessler et al. |
| 5,876,434 A | 3/1999 | Flomenblit et al. |
| 5,885,258 A | 3/1999 | Sachdeva et al. |
| 5,902,317 A | 5/1999 | Kleshinski et al. |
| 5,957,949 A | 9/1999 | Leonhardt et al. |
| 6,004,347 A | 12/1999 | McNamara et al. |
| 6,004,348 A | 12/1999 | Banas et al. |
| 6,014,589 A | 1/2000 | Farley et al. |
| 6,027,525 A | 2/2000 | Suh et al. |
| 6,033,398 A | 3/2000 | Farley et al. |
| 6,036,687 A | 3/2000 | Laufer et al. |
| 6,042,606 A | 3/2000 | Frantzen |
| 6,053,896 A | 4/2000 | Wilson et al. |
| 6,071,277 A | 6/2000 | Farley et al. |
| 6,080,160 A | 6/2000 | Chen et al. |
| 6,086,610 A | 7/2000 | Duerig et al. |
| 6,113,612 A * | 9/2000 | Swanson et al. ........... 623/1.15 |
| 6,120,534 A | 9/2000 | Ruiz |
| 6,129,758 A | 10/2000 | Love |
| 6,136,025 A | 10/2000 | Barbut et al. |
| 6,139,536 A | 10/2000 | Mikus et al. |
| 6,149,660 A | 11/2000 | Laufer et al. |
| 6,162,245 A | 12/2000 | Jayaraman |
| 6,179,878 B1 | 1/2001 | Duerig et al. |
| 6,200,336 B1 | 3/2001 | Pavenik et al. |
| 6,221,102 B1 | 4/2001 | Baker et al. |
| 6,224,626 B1 | 5/2001 | Steinke |
| 6,231,561 B1 | 5/2001 | Frazier et al. |
| 6,254,564 B1 | 7/2001 | Wik et al. |
| 6,258,118 B1 | 7/2001 | Baum et al. |
| 6,287,339 B1 | 9/2001 | Vasques et al. |
| 6,290,721 B1 | 9/2001 | Heath |
| 6,299,636 B1 | 10/2001 | Schmitt et al. |
| 6,299,637 B1 | 10/2001 | Shaolian et al. |
| 6,302,917 B1 | 10/2001 | Dua et al. |
| 6,309,416 B1 | 10/2001 | Swanson et al. |
| 6,425,915 B1 | 7/2002 | Khosravi et al. |
| 6,440,163 B1 | 8/2002 | Swanson et al. |
| 6,454,799 B1 | 9/2002 | Schreck |
| 6,503,272 B2 | 1/2003 | Duerig et al. |
| 6,511,491 B2 | 1/2003 | Grudem et al. |
| 6,527,800 B1 | 3/2003 | McGuckin et al. |
| 6,572,646 B1 | 6/2003 | Boylan et al. |
| 6,582,461 B1 | 6/2003 | Burmeister et al. |
| 6,626,899 B2 | 9/2003 | Houser et al. |
| 6,635,080 B1 | 10/2003 | Lauterjung et al. |
| 6,695,878 B2 * | 2/2004 | McGuckin et al. ......... 623/1.19 |
| 6,733,525 B2 | 5/2004 | Yang et al. |
| 6,740,111 B1 | 5/2004 | Lauterjung |
| 7,007,698 B2 | 3/2006 | Thornton |
| 7,041,128 B2 | 5/2006 | McGuckin et al. |
| 7,833,262 B2 * | 11/2010 | McGuckin, Jr. ........ A61F 2/82 623/1.18 |
| 8,109,990 B2 | 2/2012 | Paul et al. |
| 8,348,997 B2 | 1/2013 | Thompson et al. |
| 2001/0005787 A1 | 6/2001 | Oz et al. |
| 2001/0039432 A1 | 11/2001 | Whitcher et al. |
| 2002/0002401 A1 | 1/2002 | McGuckin et al. |
| 2002/0032481 A1 | 3/2002 | Gabbay |
| 2002/0055772 A1 | 5/2002 | McGuckin et al. |
| 2002/0138129 A1 | 9/2002 | Armstrong et al. |
| 2003/0018294 A1 | 1/2003 | Cox |
| 2003/0199987 A1 | 10/2003 | Berg et al. |
| 2004/0098098 A1 | 5/2004 | McGuckin, Jr. et al. |
| 2004/0220593 A1 | 11/2004 | Greenhalgh |
| 2005/0049692 A1 | 3/2005 | Numamoto et al. |
| 2006/0122692 A1 | 6/2006 | Gilad et al. |
| 2006/0149360 A1 | 7/2006 | Schwammenthal et al. |
| 2006/0190074 A1 | 8/2006 | Hill et al. |
| 2007/0112423 A1 | 5/2007 | Chu |
| 2007/0185571 A1 | 8/2007 | Kapadia et al. |
| 2008/0221669 A1 | 9/2008 | Camilli et al. |
| 2008/0294189 A1 | 11/2008 | Moll et al. |
| 2009/0062901 A1 | 3/2009 | McGuckin, Jr. |
| 2010/0030253 A1 | 2/2010 | Harris et al. |
| 2010/0217385 A1 | 8/2010 | Thompson et al. |
| 2011/0202127 A1 | 8/2011 | Mauch et al. |

FOREIGN PATENT DOCUMENTS

| | | |
|---|---|---|
| EP | 20061894543 | 3/2008 |
| WO | WO 9740755 | 11/1997 |
| WO | WO 9819629 | 5/1998 |
| WO | WO 9956655 | 11/1999 |
| WO | WO 0128459 | 4/2001 |
| WO | 0149213 | 7/2001 |
| WO | WO02100297 | 12/2002 |
| WO | 2006004679 | 1/2006 |

(56) References Cited

FOREIGN PATENT DOCUMENTS

| WO | 2007/067942 | 6/2007 |
|---|---|---|
| WO | WO2007067942 | 6/2007 |
| WO | WO 2008/100382 | 8/2008 |

* cited by examiner

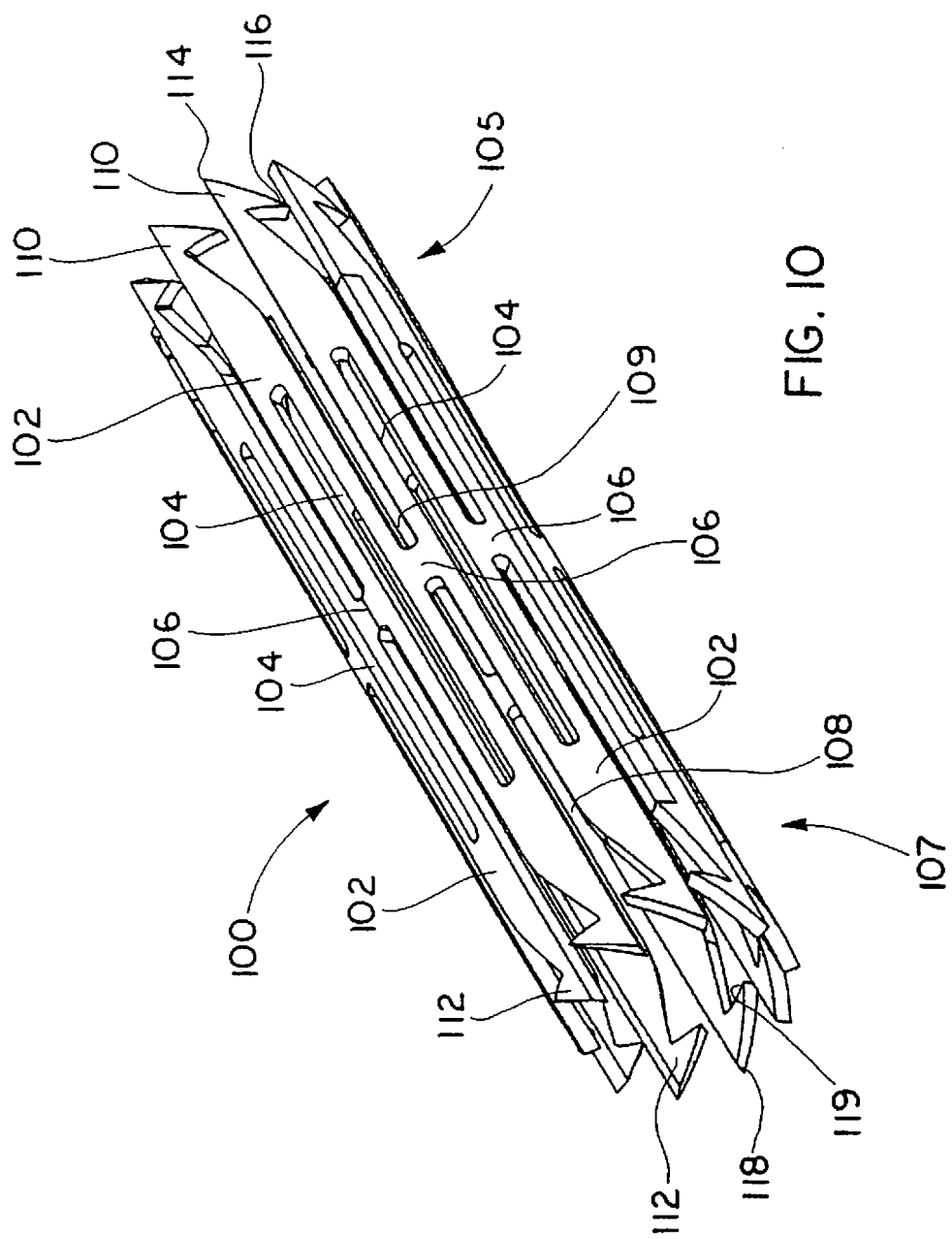

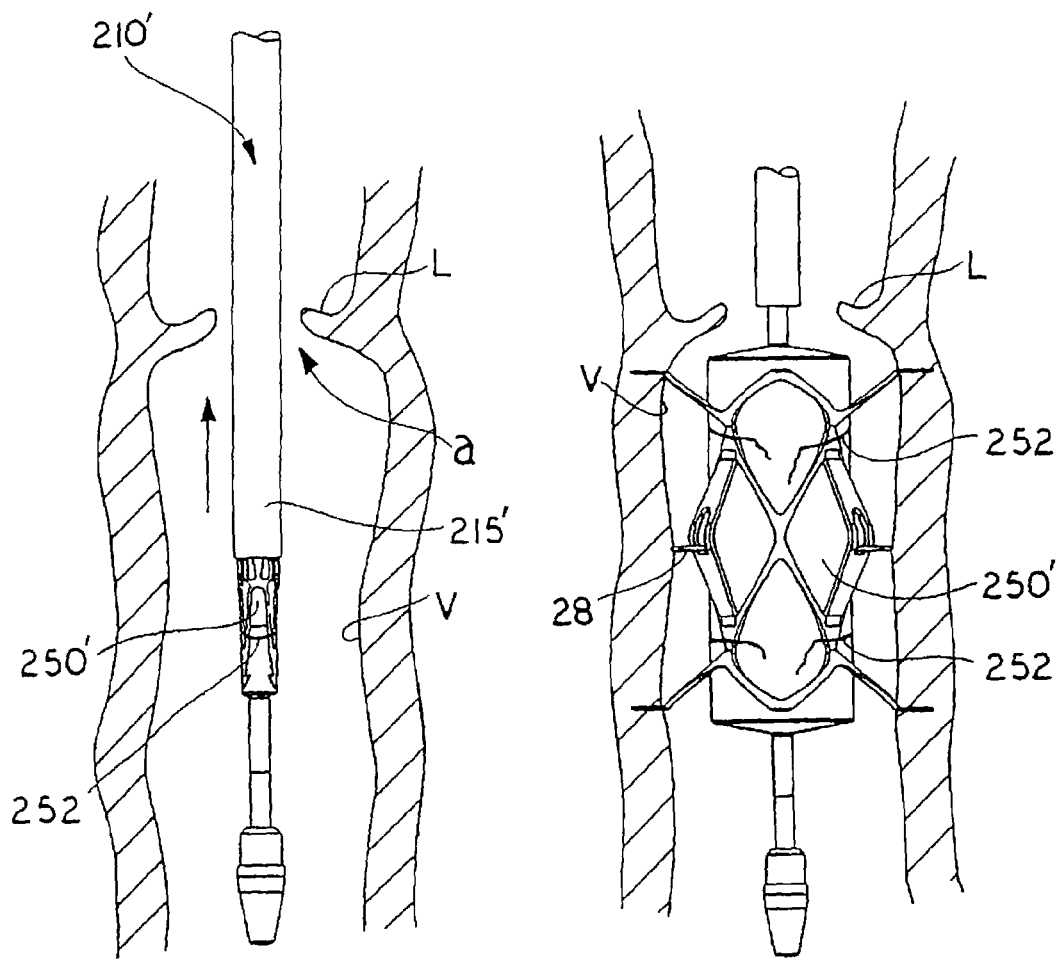
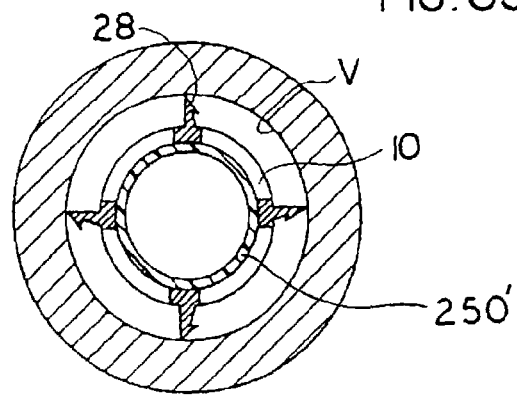
FIG. 32    FIG. 33
FIG. 34

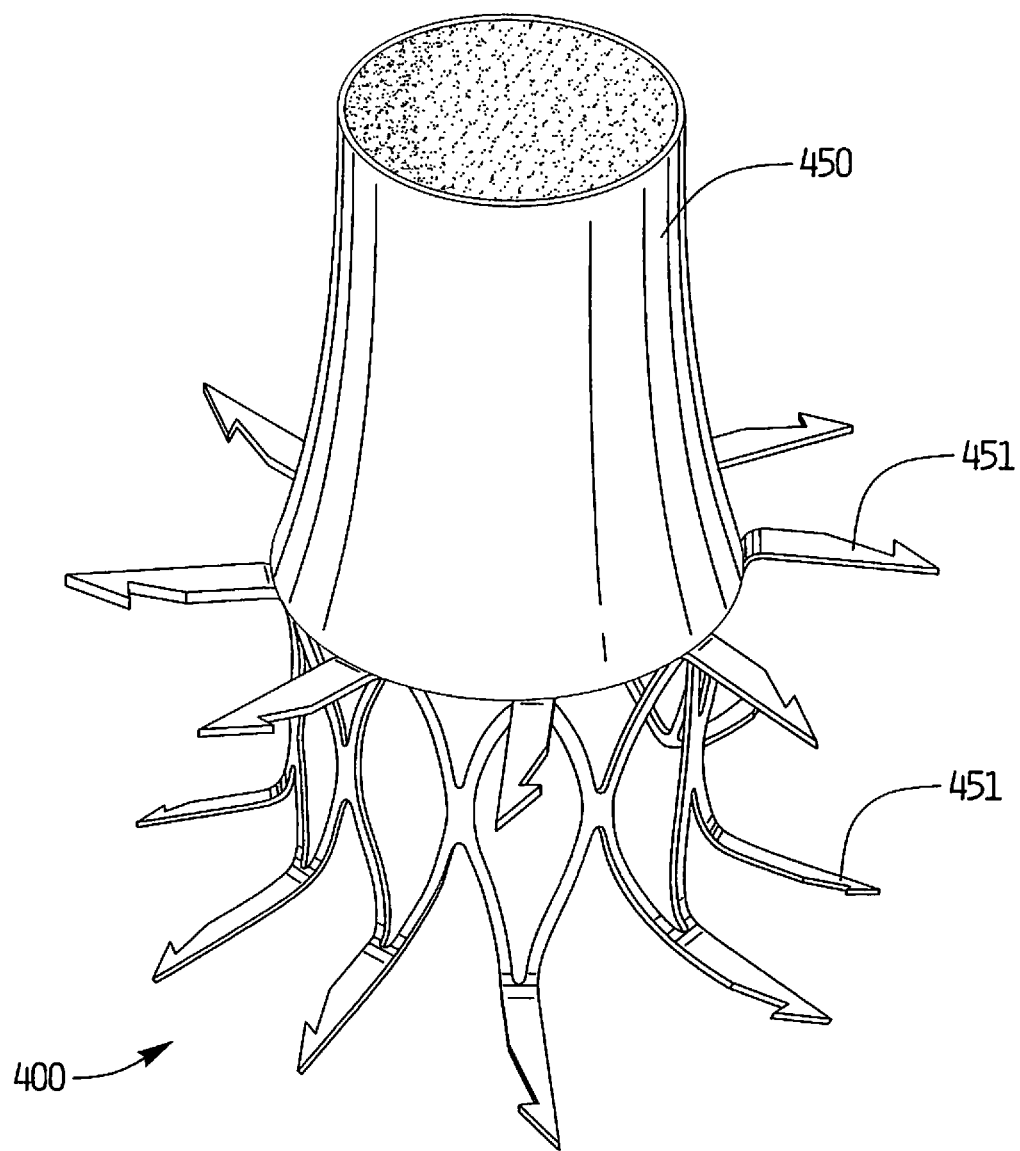
FIG_35A

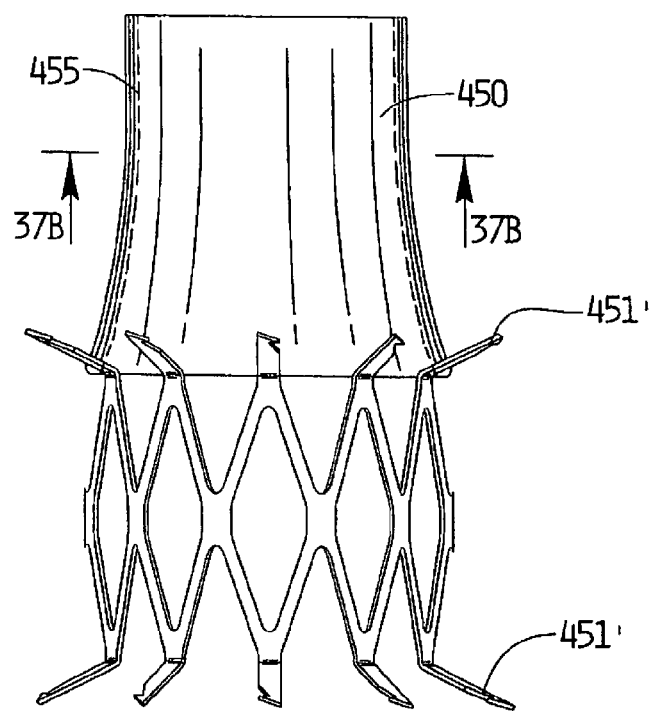
FIG_36B
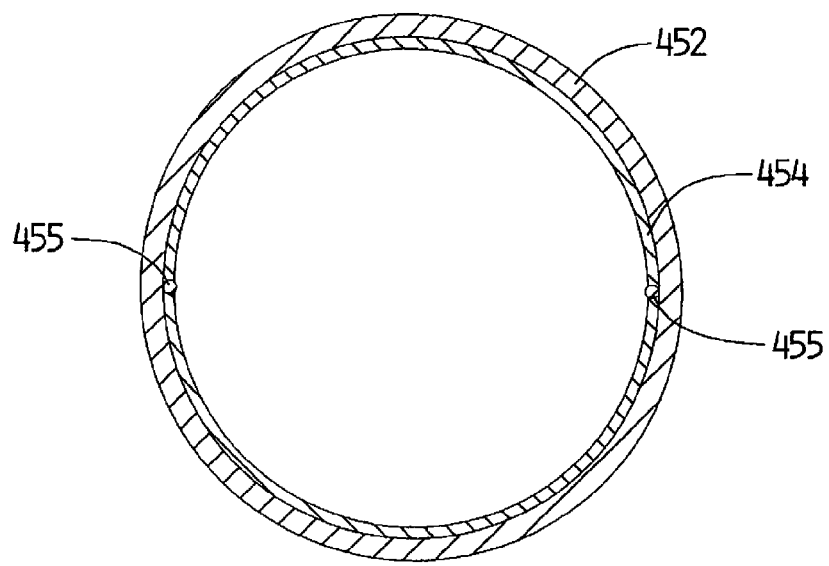
FIG_37B

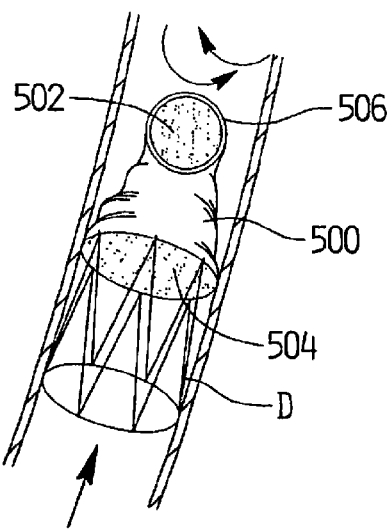
FIG_38A
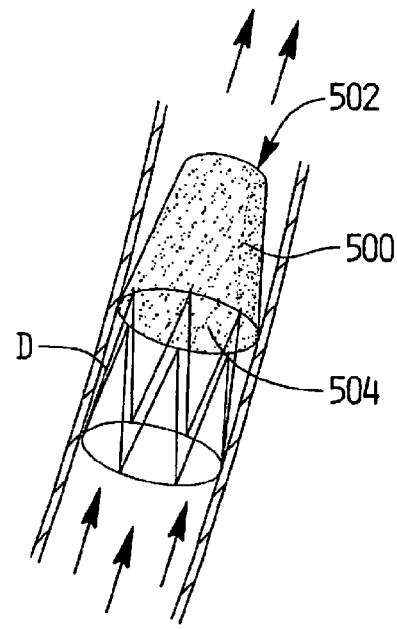
FIG_38B
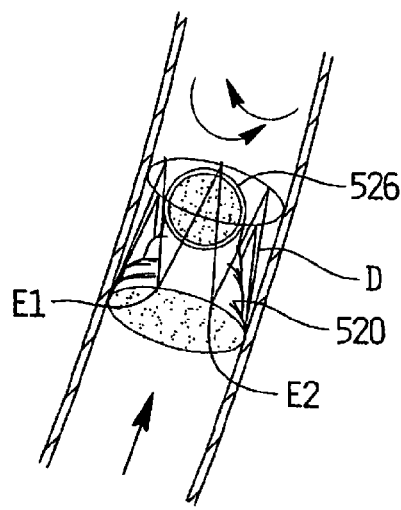
FIG_39A
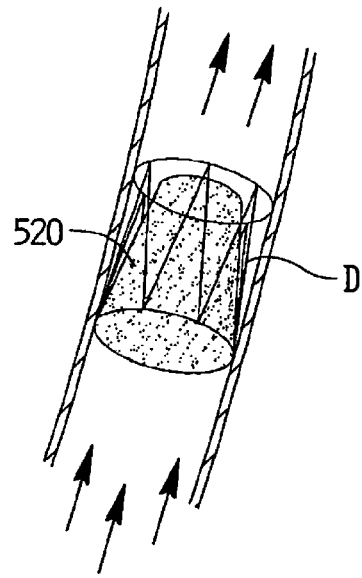
FIG_39B

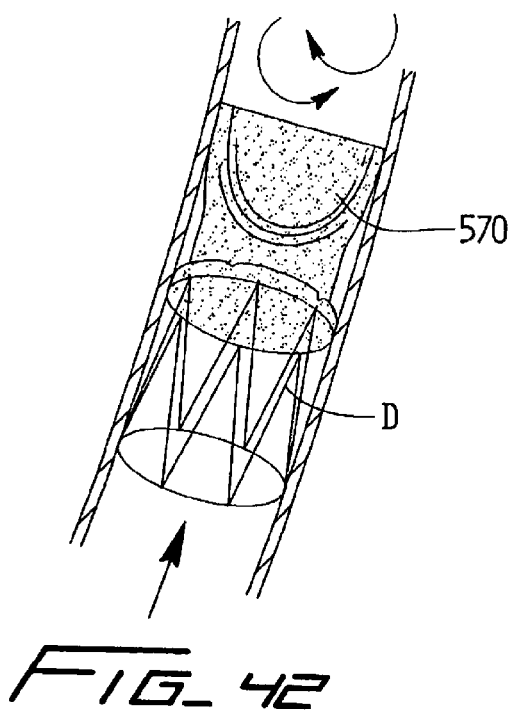
FIG_42
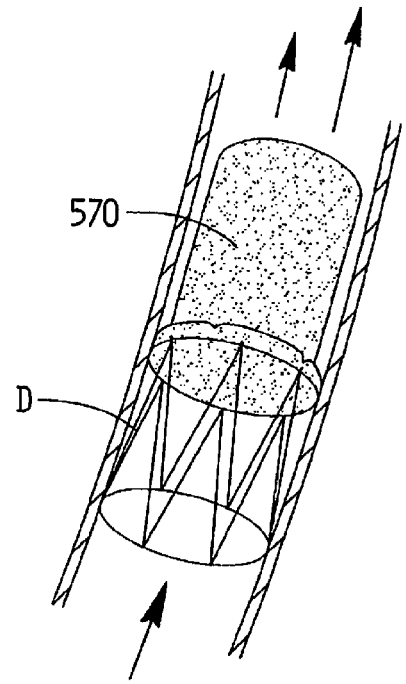
FIG_43
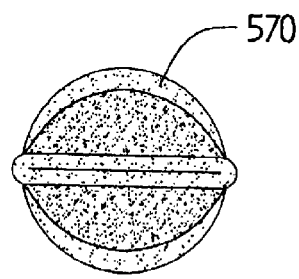
FIG_44

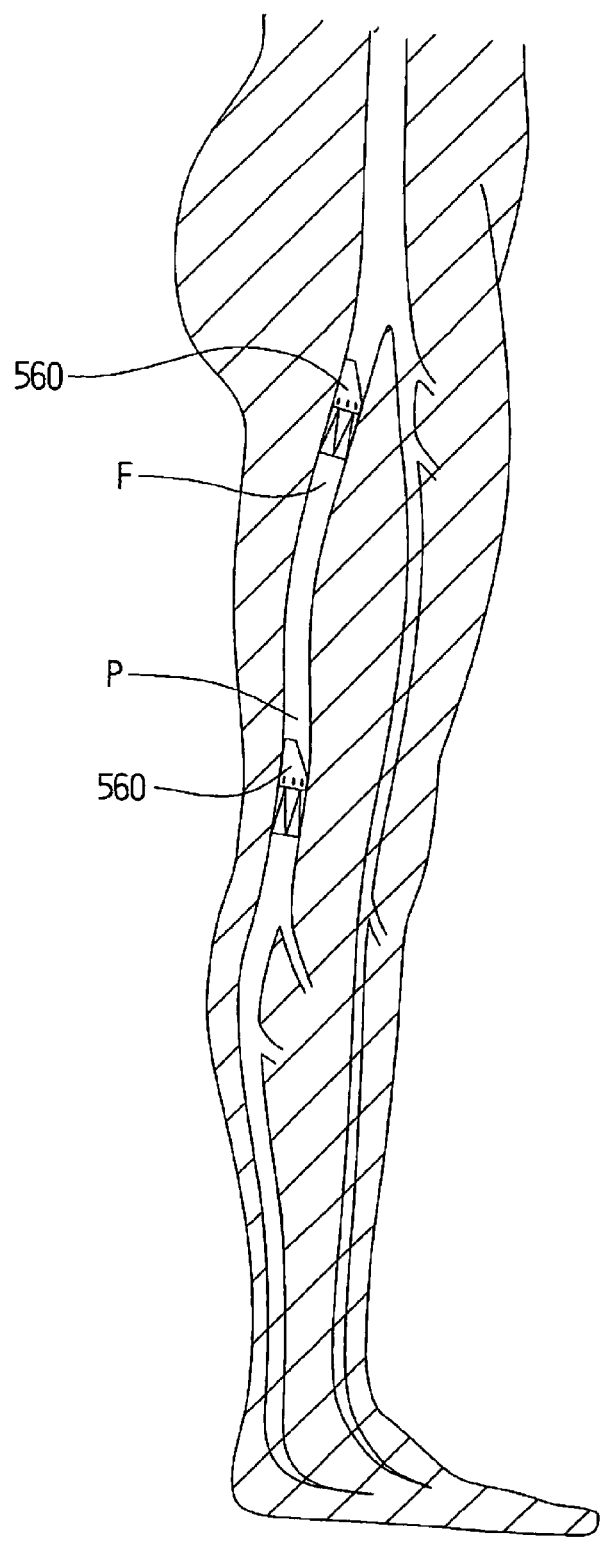
FIG_45

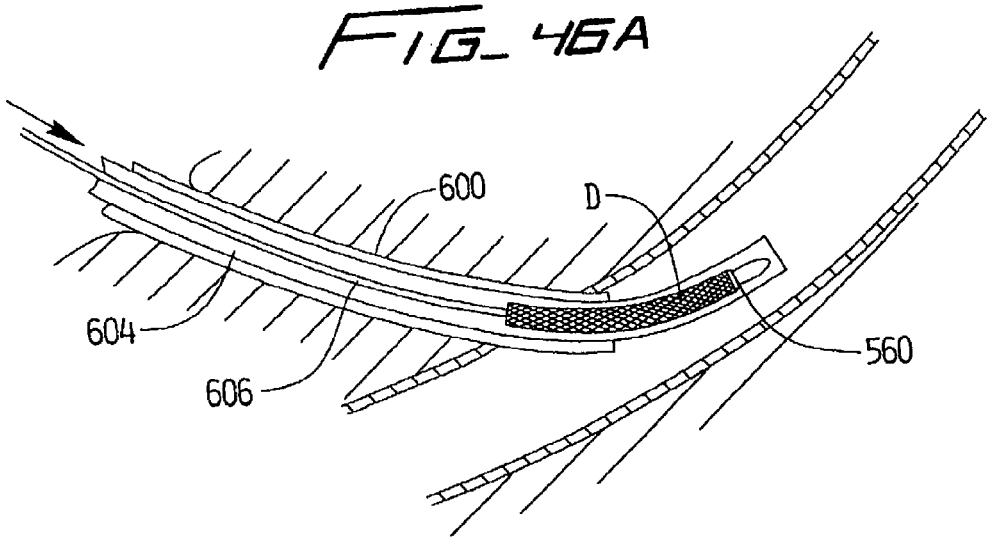
FIG_46A
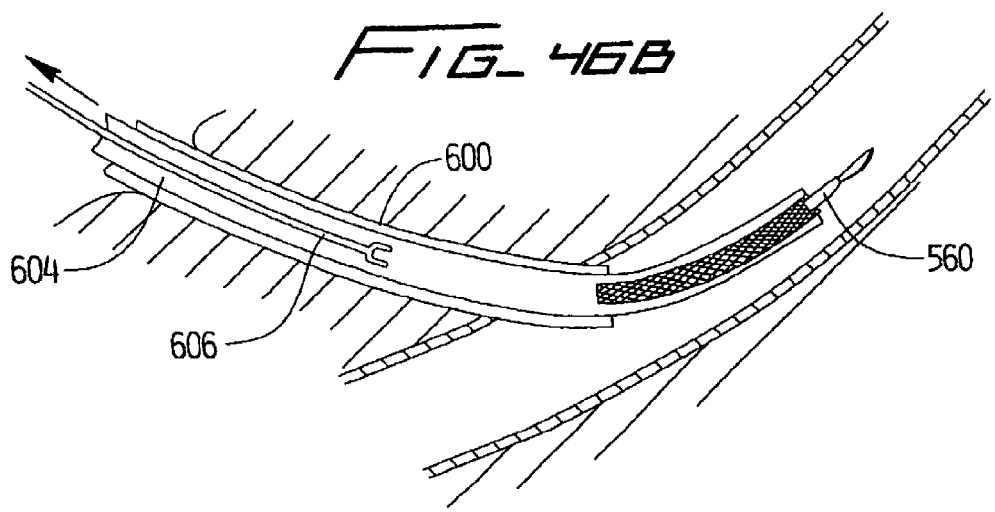
FIG_46B
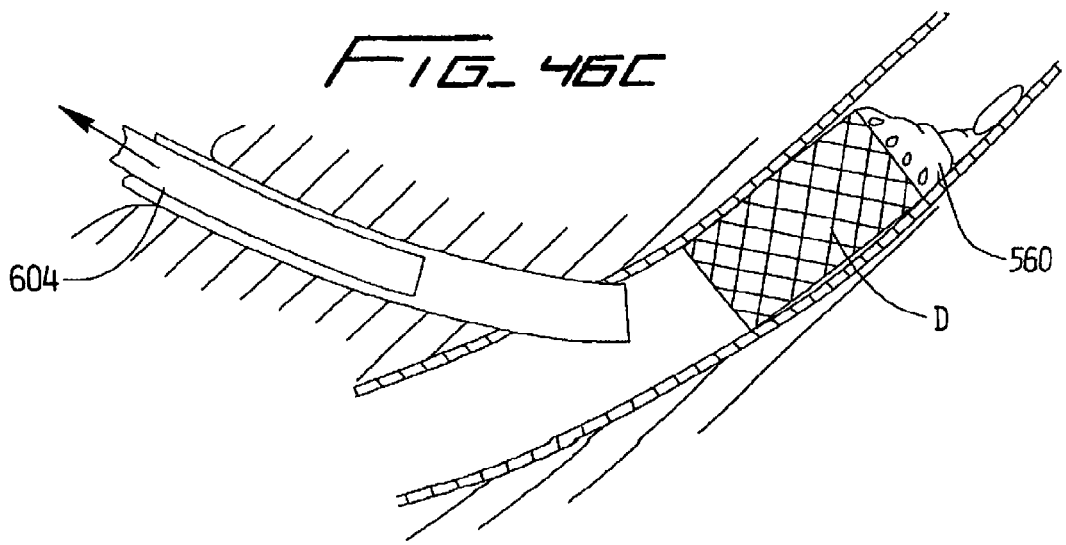
FIG_46C

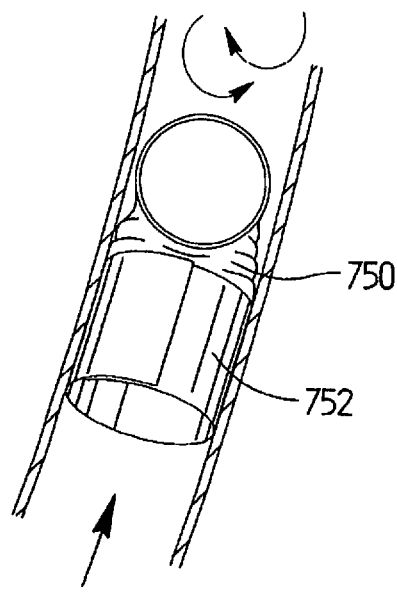
FIG_50
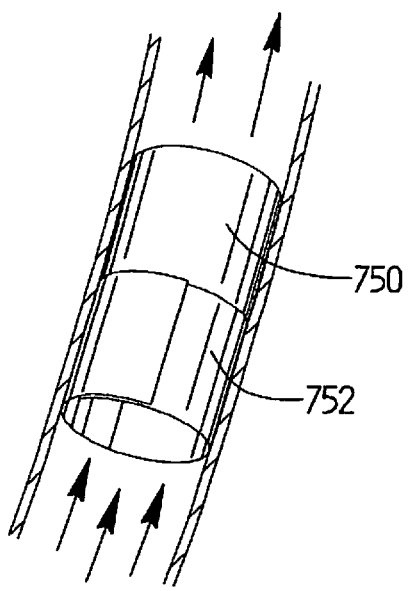
FIG_51
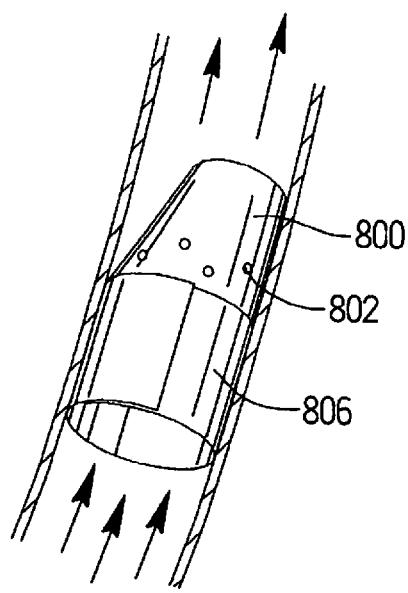
FIG_52
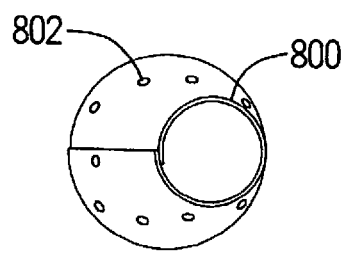
FIG_53

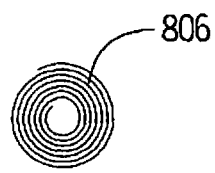
FIG_54A
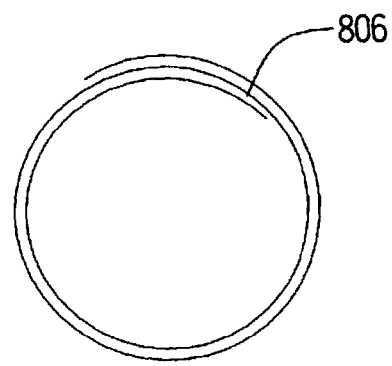
FIG_54B
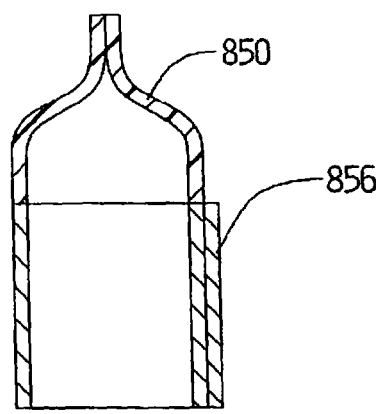
FIG_55

VASCULAR DEVICE WITH VALVE FOR APPROXIMATING VESSEL WALL

This application is a continuation of patent application Ser. No. 12/880,499 filed on Sep. 13, 2010, which is a continuation of patent application Ser. No. 10/706,685 filed on Nov. 12, 2003, now U.S Pat. No. 7,833,262, which is a divisional of application Ser. No. 10/011,345 filed on Dec. 5, 2001 now U.S Pat. No. 6,676,698, which claims benefit of provisional application No. 60/317,801 filed on Sep. 7, 2001 and is a continuation-in-part of U.S patent application Ser. No. 09/877,639 filed Jun. 8, 2001, now U.S Pat. No. 6,695,878, and a continuation-in-part of U.S patent application Ser. No. 09/877,480 filed Jun. 8, 2001, now U.S Pat. No. 6,527,800, both of which claim priority from U.S Provisional patent application No. 60/214,120 filed on Jun. 26, 2000. The entire contents of each of these applications are incorporated herein by reference.

BACKGROUND

Technical Field

This application relates to a vascular device and more particularly to a vascular device for approximating the vessel wall and placing a valve for treating venous valve insufficiency.

Background of Related Art

Veins in the body transport blood to the heart and arteries carry blood away from the heart. The veins have one-way valve structures in the form of leaflets disposed annularly along the inside wall of the vein which open to permit blood flow toward the heart and close to prevent back flow. That is, when blood flows through the vein, the pressure forces the valve leaflets apart as they flex in the direction of blood flow and move towards the inside wall of the vessel, creating an opening therebetween for blood flow. The leaflets, however, do not normally bend in the opposite direction and therefore return to a closed position to prevent blood flow in the opposite, i.e. retrograde, direction after the pressure is relieved. The leaflet structures, when functioning properly, extend radially inwardly toward one another such that the tips contact each other to block backflow of blood.

In the condition of venous valve insufficiency, the valve leaflets do not function properly as they thicken and lose flexibility, resulting in their inability to extend sufficiently radially inwardly to enable their tips to come into sufficient contact with each other to prevent retrograde blood flow. The retrograde blood flow causes the buildup of hydrostatic pressure on the residual valves and the weight of the blood dilates the wall of the vessel. Such retrograde blood flow, commonly referred to as reflux, leads to swelling and varicose veins, causing great discomfort and pain to the patient. Such retrograde blood flow, if left untreated can also cause venous stasis ulcers of the skin and subcutaneous tissue. There are generally two types of venous valve insufficiency: primary and secondary. Primary venous valve insufficiency is typically a condition from birth, where the vein is simply too large in relation to the leaflets so that the leaflets cannot come into adequate contact to prevent backflow. More common is secondary venous valve insufficiency which is caused by clots which gel and scar, thereby changing the configuration of the leaflets, i.e. thickening the leaflets creating a "stub-like" configuration. Venous valve insufficiency can occur in the superficial venous system, such as the saphenous veins in the leg, or in the deep venous system, such as the femoral and popliteal veins extending along the back of the knee to the groin.

A common method of treatment of venous valve insufficiency is placement of an elastic stocking around the patient's leg to apply external pressure to the vein, forcing the walls radially inwardly to force the leaflets into apposition. Although sometimes successful, the tight stocking is quite uncomfortable, especially in warm weather, as the stocking must be constantly worn to keep the leaflets in apposition. The elastic stocking also affects the patient's physical appearance, thereby potentially having an adverse psychological affect. This physical and/or psychological discomfort sometimes results in the patient remove the stocking, thereby preventing adequate treatment.

Another method of treatment has been developed to avoid the discomfort of the stocking. This method involves major surgery requiring the implantation of a cuff internally of the body, directly around the vein. This surgery requires a large incision, resulting in a long patient recovery time, scarring and carries the risks, e.g. anesthesia, inherent with surgery.

Another invasive method of surgery involves selective repairing of the valve leaflets, referred to as valvuloplasty. In one method, sutures are utilized to bring the free edges of the valve cusp into contact. This procedure is complicated and has the same disadvantages of the major surgery described above.

Co-pending, commonly assigned U.S. patent application Ser. Nos. 09/877,639 and 09/877,480, incorporated herein by reference, disclose an advantageous method and device to minimally invasively treat venous valve insufficiency without requiring an outer stocking or internal cuff. Such device avoids the physical and psychological discomfort of an external stocking as well as avoids the risk, complexity and expense of surgically implanted cuffs. The device is advantageously inserted minimally invasively, i.e. intravascularly, and functions to effectively bring the valve leaflets into apposition. This device first expands against the vessel wall to grasp the wall, and then contracts to bring the vessel wall radially inwardly so the leaflets can be pulled closer together to a functional position. The present application utilizes the device of these prior applications for bringing the vessel wall radially inwardly to correct the dilation of the wall, but rather than rely on the patient's existing valve leaflets which may be scarred or non-functional, contains a replacement valve as a substitute for the patient's leaflets. Thus, advantageously, venous valve insufficiency can be treated minimally invasively by bringing the vessel wall inwardly and replacing the patient's valve.

SUMMARY

The present invention provides a vascular device comprising a plurality of vessel engaging members and a valve. The device is movable from a collapsed insertion position having a first diameter to a second expanded position having a second diameter larger than the first diameter. The plurality of vessel engaging members extend outwardly from the device for securely engaging the internal wall of a vessel upon expansion of the device to the second expanded position, wherein the vessel engaging members pull the internal wall of the vessel radially inwardly upon movement of the device from the second expanded position toward a first expanded position having a third diameter. This third diameter is greater than the first diameter and less than the second diameter. In the first expanded position the valve is movable between an open position to allow blood flow therethrough to a closed position to prevent blood flow.

The device is preferably composed of shape memory material and preferably the first expanded position substantially corresponds to the memorized position of the device. The device is expanded to the second expanded position by an expandable device, such as a balloon, positioned within the device.

In one embodiment, the device is initially movable from the collapsed position to the first expanded position in response to exposure to body temperature, and is subsequently moved from the first expanded position to the second expanded position by an expandable member. In another embodiment, the device is movable from the collapsed position to the second expanded position by the substantial simultaneous exposure to body temperature and expansion by an expandable member.

The present invention also provides a vascular system comprising a balloon catheter having an elongated shaft and an expandable balloon, a vascular device mounted over the expandable balloon and having a first position and a second expanded position, and a valve connected to the vascular device and movable between a closed position to prevent blood flow and an open position to allow blood flow therethrough. The vascular device is expandable to the expanded position to engage the vessel walls and returnable substantially to the first position to bring the walls radially inwardly.

The vascular device in one embodiment comprises a shape memory material and can be expandable first to a memorized condition in response to exposure to body temperature and subsequently expanded to the expanded position by inflation of the balloon. Alternatively, the vascular device can be expandable to the expanded position as the device is substantially simultaneously exposed to body temperature and the balloon is inflated. The device in another embodiment can be composed of stainless steel and is expandable by the balloon below its elastic limit to enable return of the device to the first position.

In the foregoing devices and system, the vascular device can be releasably connected to the balloon. The valve can be attached to a distal end of the vascular device to extend downstream of the device when positioned within a patient. Alternatively, the valve can be attached to a proximal end of the vascular device to extend within a central portion of the device when positioned within a patient. The valve is preferably substantially conical in shape. The valve can alternatively have a duckbill valve configuration. In one embodiment, a longitudinal axis of the valve is offset from a longitudinal axis of the vascular device. The valve may include a plurality of blood drainage openings extending through a side wall. A reinforcement ring can be provided adjacent the distal opening.

The present invention also provides a method for treating venous valve insufficiency comprising:

inserting a delivery device and a vascular device having a replacement valve into a target vessel adjacent the region of the removed portion of leaflets;

deploying the vascular device to an enlarged diameter to securely engage the internal wall of the vessel; and reducing the diameter of the vascular device to move the vessel wall radially inwardly to reduce dilation of the vessel and implant the replacement valve.

The method can further include the step of removing at least a portion of vein valve leaflets of a patient before inserting the vascular device.

In one embodiment, the method further comprises the step of deploying the vascular device to a first expanded diameter prior to deploying the device to the enlarged diameter, the first expanded diameter being less than the enlarged diameter, and the step of reducing the diameter of the vascular device returns the device to a diameter substantially equal to the first expanded diameter. In this embodiment, the step of deploying the vascular device to a first diameter preferably comprises the step of exposing the vascular device from a sheath of the delivery device to enable the vascular device to return a shape memorized configuration in response to being warmed by body temperature. The step of the deploying the vascular device to an enlarged diameter in this embodiment preferably includes the step of inflating a balloon positioned within the device.

Alternatively the step of deploying the vascular device to an enlarged diameter comprises releasing the vascular device from the delivery device to enable it to return to a shape memorized condition and substantially simultaneously inflating a balloon.

The delivery device can be inserted through the jugular vein or femoral vein into the popliteal vein or the saphenous vein.

Replacement Valve

In another aspect, the present invention provides a replacement valve comprising a support structure and a valve attached thereto, the valve being substantially conical in configuration and having a distal opening facing away from the longitudinal axis when the valve is in the closed position and aligned with the longitudinal axis when the valve is in the open position.

In one embodiment the valve is attached to a proximal end of the support structure, and in another embodiment the valve is attached to a distal end of the support structure. In one embodiment, the valve is offset with respect to the longitudinal axis of the support structure. The valve can optionally include a plurality of drainage openings formed in a side wall adjacent the proximal end.

BRIEF DESCRIPTION OF THE DRAWINGS

Preferred embodiment(s) of the present disclosure are described herein with reference to the drawings wherein:

FIG. 10 is a perspective view of the vascular device of FIG. 8 in the collapsed configuration for delivery within the vessel;

FIG. 21B corresponds to the position of the vascular device in FIG. 19 wherein the balloon has been inflated to radially expand the device to a second expanded position to enable the vessel engaging members to penetrate the vessel wall; and FIG. 21C corresponds to the position of the vascular device in FIG. 20 wherein the balloon has been deflated and the device returns to the first expanded position bringing the vessel wall radially inwardly;

FIG. 32 is a side view of an alternate embodiment of the delivery system of the present invention having a restraint, the view being similar to FIG. 23 in showing the vascular device expanded within the vessel, upstream of the valve leaflets, after the sheath has been withdrawn;

FIG. 33 is a view similar to FIG. 32, showing the vascular device of FIG. 1 expanded by a balloon so the vessel engaging members penetrate and retain the vessel wall, and the restraint being severed by expansion of the balloon;

FIG. 34 is a transverse cross-sectional view of the vascular device of FIG. 1 with the restraint of FIG. 32 shown expanded to the memorized position substantially simultaneously with expansion of the balloon;

FIG. 35A is a perspective view of the vascular device of the present invention having a first embodiment of a replacement valve attached thereto, the device being shown in the expanded position and the valve shown in the open position;

FIG. 36B is a side view of the vascular device similar to FIG. 36A except showing the alternate embodiment of the vascular device having angled vessel engaging members;

FIG. 37B is a transverse cross-sectional view of the vascular device of FIG. 37A;

FIG. 38A is a perspective view of a second embodiment of the replacement valve of the present invention shown in the closed position to prevent blood flow therethrough, the vascular device being shown schematically;

FIG. 38B is perspective view of the valve of FIG. 38A in the open position to enable blood flow;

FIG. 39A is a perspective view of a third embodiment of the replacement valve of the present invention shown in the closed position to prevent blood flow therethrough, the vascular device being shown schematically;

FIG. 39B is perspective view of the valve of FIG. 39A in the open position to enable blood flow;

FIG. 42 is a perspective view of a sixth embodiment of the replacement valve of the present invention, in the form of a duckbill valve, shown in the closed position to prevent blood flow therethrough, the vascular device being shown schematically;

FIG. 43 is perspective view of the valve of FIG. 42 in the open position to enable blood flow;

FIG. 44 is a top view of the valve of FIG. 42;

FIG. 45 is a schematic view of two vascular devices with the offset valves of FIG. 41 inserted in the popliteal and femoral vein of a patient;

FIGS. 46A-46C illustrate sequentially the steps of insertion of the vascular device shown schematically with the offset valve of FIG. 41 inserted into the popliteal vein wherein FIG. 46A shows advancement of the delivery catheter and valve through introducer sheath;

FIG. 46B shows withdrawal of the pusher from the delivery catheter to release the vascular device;

FIG. 46C shows withdrawal of the delivery catheter for expansion and placement of the vascular device;

FIGS. 47A-47C illustrate sequentially the steps of inserting a grasper to reposition the vascular device wherein FIG. 47A illustrates the grasper and outer tube inserted through the introducer sheath to access the vascular device;

FIG. 47B illustrates advancement of the prongs from the outer tube towards the vascular device; and FIG. 47C illustrates the vascular device grasped and moved proximally by the prongs to a different location;

FIG. 50 is perspective view of a first embodiment of a vascular device in the form of an expandable cylinder and having an eighth embodiment of the replacement valve attached thereto, the valve shown in the closed position;

FIG. 51 is a perspective view of the valve of FIG. 50 in the open position to enable blood flow;

FIG. 52 is a perspective view of the vascular device of FIG. 50 having a ninth embodiment of a replacement valve attached thereto, the valve shown in the open position;

FIG. 53 is a top view of the vascular device and valve of FIG. 52;

FIG. 54A is a bottom view of the vascular device of FIG. 52 shown in the expanded position;

FIG. 54B is a bottom view of the vascular device in FIG. 52 shown in the retracted position; and FIG. 55 is a cross-sectional view of a tenth embodiment of a replacement valve in the form of an expandable cylinder having a duckbill valve.

DETAILED DESCRIPTION OF PREFERRED EMBODIMENTS

Figure 1:
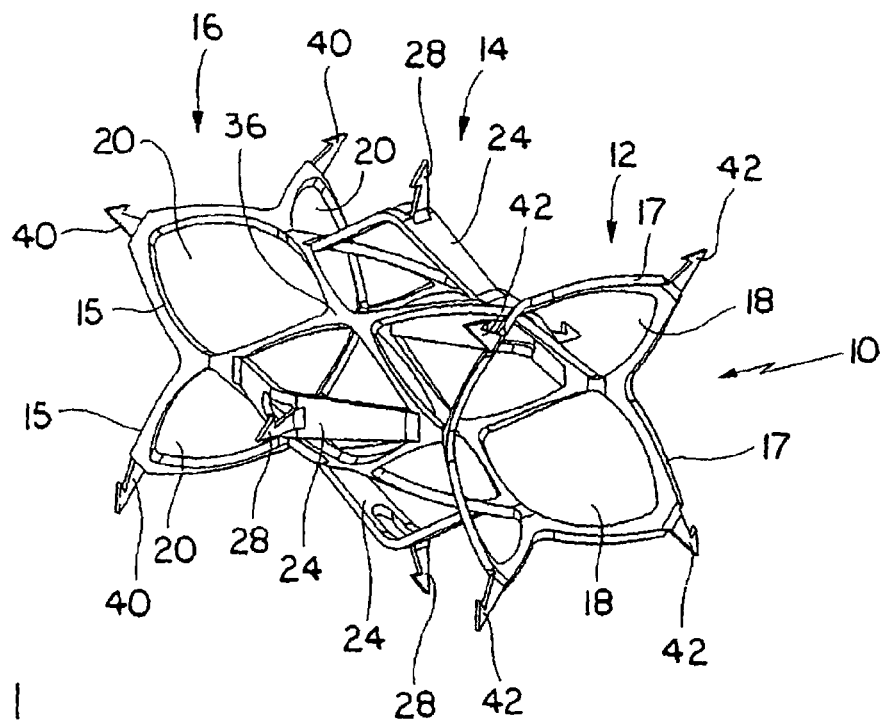
FIG. 1 is a perspective view of a first embodiment of the vascular device of the present invention shown in the expanded configuration.
Figure 2:
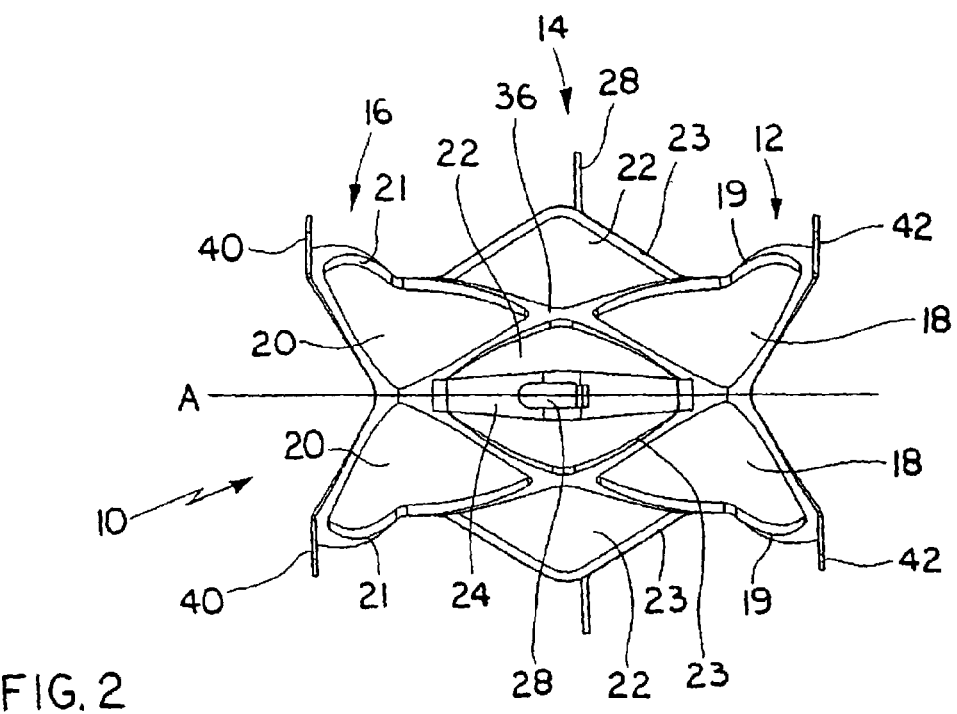
FIG. 2 is a side view of the vascular device of FIG. 1 in the expanded configuration.
Figure 3:
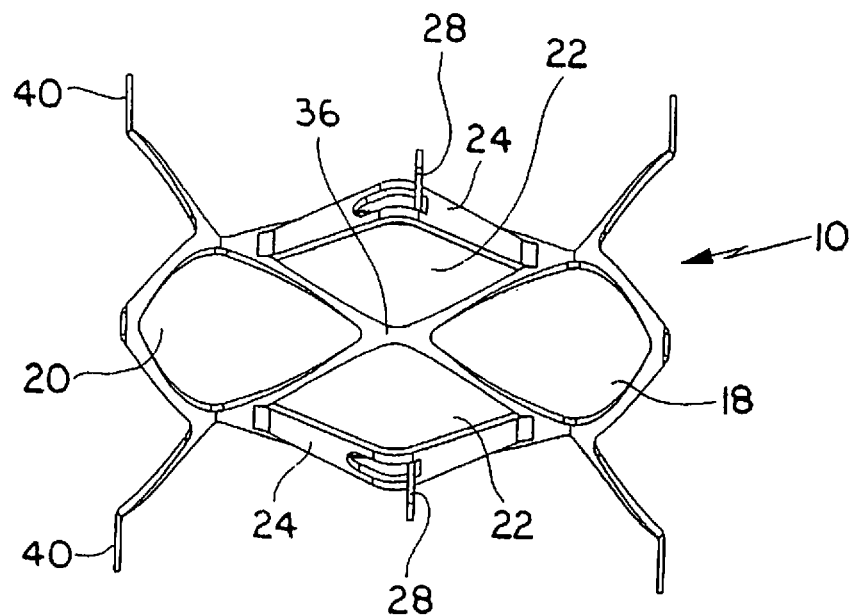
FIG. 3 is another side view of the vascular device in the expanded configuration, rotated 45 degrees with respect to FIG. 2.
Figure 4:
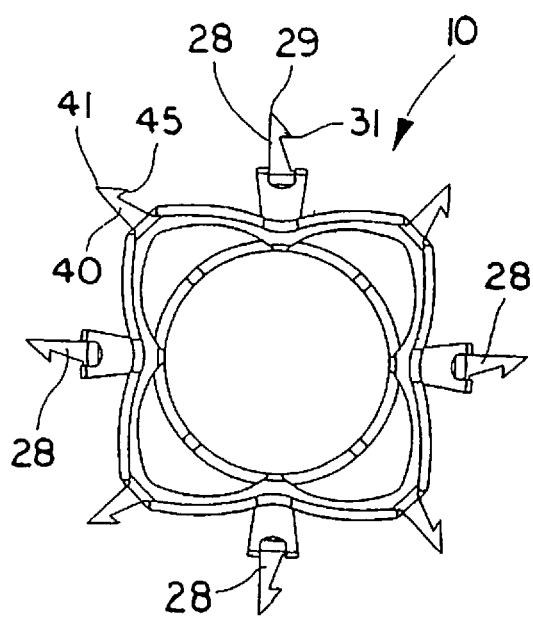
FIG. 4 is a front view of the vascular device of FIG. 1 in the expanded configuration.

Referring now in detail to the drawings where like reference numerals identify similar or like components throughout the several views, FIGS. 1-7 illustrate a first embodiment of the vascular device of the present invention and FIGS. 8-11 illustrate a second embodiment of the vascular device of the present invention. The devices, designated generally by reference numerals 10 and 100, are expanded to engage the internal wall of the vessel and contracted to pull the vessel walls radially inwardly. By pulling the vessel wall radially inwardly, the valve leaflets within the vessel are pulled closer together to a functional condition.

Figure 5:
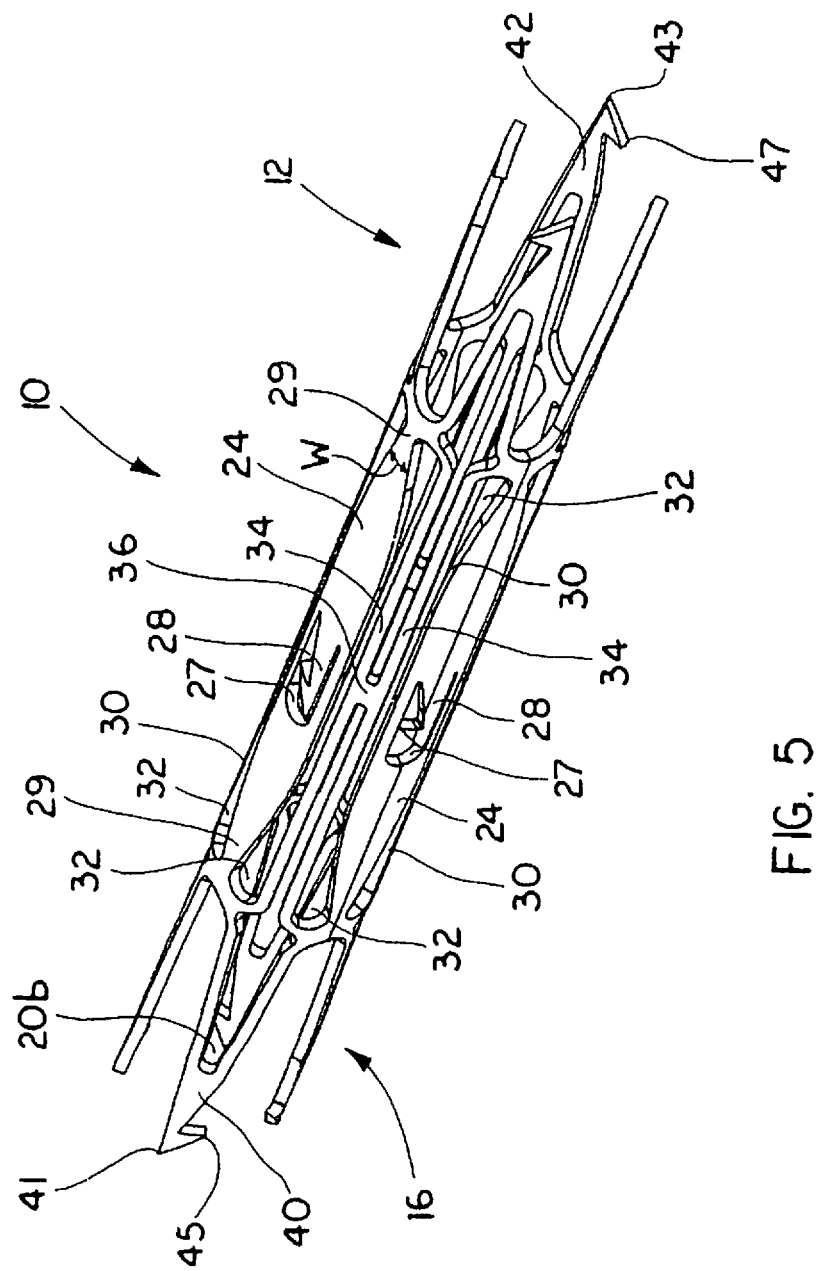
FIG. 5 is a perspective view of the vascular device of FIG. 1 shown in the collapsed configuration for delivery within the vessel.
Figure 6:
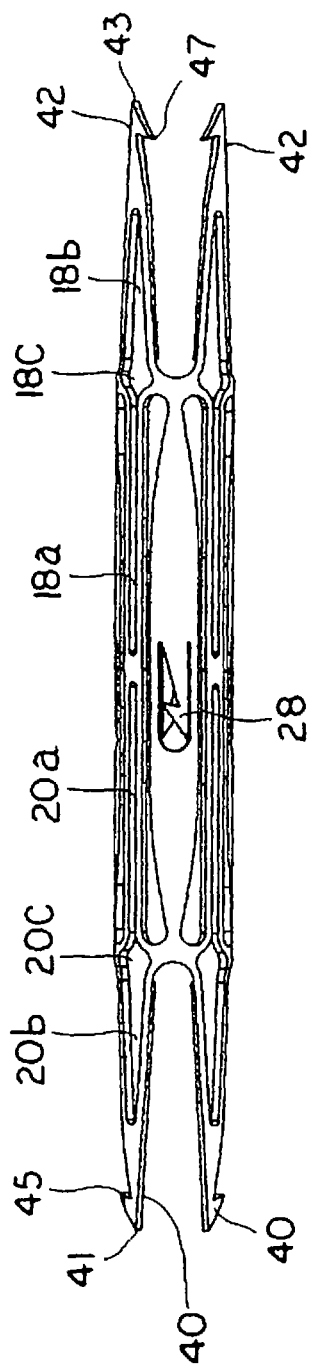
FIG. 6 is a side view of the vascular device of FIG. 1 in the collapsed configuration.
Figure 7:
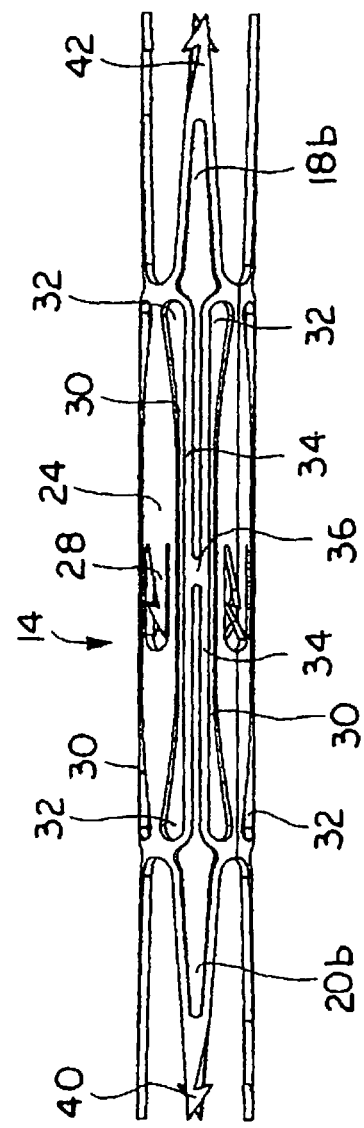
FIG. 7 is another side view of the vascular device in the collapsed configuration, rotated 45 degrees with respect to FIG. 6.

FIGS. 1-4 illustrate vascular device 10 of the first embodiment in the expanded configuration and FIGS. 5-7 illustrate vascular device 10 in the collapsed configuration. Vascular device 10 is preferably composed of a shape memory material, such as a nickel-titanium alloy commonly known as Nitinol, so that in its memorized configuration it assumes the shape shown in FIG. 1. This shape memory material characteristically exhibits rigidity in the austenitic state and more flexibility in the martensitic state. To facilitate passage from the delivery catheter, the shape memory device is maintained in a collapsed configuration inside a delivery sheath as described in more detail below, where it is cooled by a saline solution to maintain the device below its transition temperature. The cold saline maintains the temperature dependent device in a relatively softer condition as it is in the martensitic state within the sheath. This facilitates the exit of device 10 from the sheath as frictional contact between the device and the inner wall of the sheath would otherwise occur if the device was maintained in a rigid, i.e. austenitic, condition. When the device 10 is released from the sheath to the target site, it is warmed by body temperature, thereby transitioning in response to this change in temperature to an austenitic expanded condition.

Device 10 is preferably formed from a tubular member, preferably by laser cutting. Device 10 includes a proximal portion 12, and intermediate portion 14 and a distal portion 16. In the expanded condition, the device 10 has four substantially diamond shaped cells 17 forming substantially diamond shaped openings 18 at the proximal portion 12 and four substantially diamond shaped cells 15 forming substantially diamond shaped openings 20 at the distal portion 16. The end regions 19 of the cells 18, and the end regions 21 of the cells 20 are bent outwardly from the plane of the remainder of the cell, in a direction away from the longitudinal axis of the vascular device 10. This better enables the vessel engaging members, described below, to engage the vessel walls.

The intermediate portion 14 is formed of four substantially diamond shaped cells forming substantially diamond shaped openings 22 arranged around a 360 degree arc of the cylindrical tubular member 10, with a longitudinal strip 24 extending through to bisect each cell. Thus, four symmetric bisected cells 23 are formed. Each longitudinal strip 24 has a vessel engaging member 28 extending therefrom to engage the vessel wall as will be described below. In the expanded condition, the longitudinal strip 24 buckles radially outwardly, away from the longitudinal axis of the vascular device 10, to enable the center vessel engaging members 28 (described below) to engage and secure the internal vessel wall.

The geometry of the vascular device 10 can also be appreciated with reference to the collapsed configuration of the vascular device 10 shown in FIG. 5-7. As shown, the device 10 is in the form of a cylinder with a reduced diameter. Each longitudinal strip 24 has a cutout 27 to form vessel engaging member 28. The longitudinal strip 24 is tapered in width "w" at its opposing ends 29 which connect to the framework. The longitudinal slot 30 on each side of the strip 24 is substantially straight and has enlarged oval-like regions 32 at opposing ends. The outer wall 34 of each longitudinal slot 30, i.e. the wall of slot 34 spaced further from the longitudinal strip 24, is joined to the outer wall 34 of an adjacent longitudinal slot 30 by transverse rib 36. Each rib 36 forms one vertex of a cell 15 and one vertex of a cell 17 when expanded. The cell openings 18 and 20 in the collapsed configuration as shown in FIG. 6, have, respectively, a narrowed elongated portion 20a, 18a, and a widened portion 20b, 18b with flared out regions 20c, 18c, to form the diamond shaped openings having bent end regions 21, 19 when device 10 is expanded. The flared out regions 20c, 18c enable the formation of such bent regions 21, 19.

A vessel engaging member extends from the framework of each of the cells 15 and 17. The vessel engaging member is preferably in the form of a hook with a penetrating tip and a barb.

More specifically, a vessel engaging member 40 extends outwardly and distally from the frame of each of the four cells 15 at the distal portion 16 of the device 10. In the collapsed configuration of device 10, each member 40 preferably extends generally parallel to the longitudinal axis of vascular device 10 and in substantially the same plane as the corresponding rib 36 at the opposing end.

Similarly, vessel engaging members 42 extend outwardly and proximally from the framework of each of the four cells 17 at the proximal portion 12 of the device 10. In the collapsed configuration of device 10, each member 42 preferably extends generally parallel to the longitudinal axis of vascular device 10 and in the same plane as the corresponding rib 36 at the opposing end The four vessel engaging members 28 formed in the middle (intermediate) portion 14 in the collapsed configuration lie substantially parallel the longitudinal axis of the device 10 and in the same plane as the longitudinal strip 24 from which it is formed.

Each of the vessel engaging members 28, 40 and 42, are preferably in the form of a hook having a penetrating tip 29, 41 and 43 to pierce the vessel wall and a barb 31, 45 and 47, respectively, to help retain the vessel wall. The sharp penetrating tips 29, 41, 43 penetrate the vessel wall in a radial direction and hold the vessel against axial movement with respect to the device 10; barbs 31, 45, 47, restrict radial movement of the vessel with respect to the device 10, thereby together securely retaining (grasping) the vessel wall for radial inward movement described below.

It should be understood that although four vessel engaging members 42, 40, 28 are described extending from the proximal and distal cells 17, 15 and from the center longitudinal strips 24, respectively, a fewer or greater number of vessel engaging members can be provided as long as they achieve the vessel retaining function as described in more detail below.

When the vascular device 10 expands, members 28, 40 and 42 are moved to a shape memorized orientation bent outwardly at an angle, preferably about 90 degrees, with respect to the longitudinal axis "A" of the device 10 with regions 19 and 21 bending out of the plane to increase the distance the members can extend from the center to the vessel wall. Longitudinal strips 24 buckle radially outwardly, and members 28 bend outwardly at an angle, preferably about 90 degrees, with respect to the longitudinal axis, to engage the vessel wall. Although 90 degree angles are shown, clearly other angles are contemplated. Note that due to the geometry of the device 10, the points at the outer edge come inwardly axially, shortening the length of the device, and the center strut (strip) 24 buckles radially outwardly. The buckling extends the radial reach of the device 10. Note also that in the expanded configuration, the tips of the vessel engaging members terminate at substantially the same distance from the longitudinal axis of the device 10. The length of the end hooks is preferably the same as the length of the middle hooks; the bent regions 19, 21 accommodate for the buckling of strut 24. Due to the laser cut configuration, foreshortening, i.e. the reduction in length of the device in response to expansion, is reduced.

By way of example, for use for instance in an unhealthy dilated vessel of 14 mm. the length of the vascular device 10 in the collapsed configuration could be about 3 cm and the outer diameter about 3.5 mm. In the memorized expanded configuration, the length decreases to about 2.8 cm and the transverse cross-sectional dimension increases to about 12 mm, 15.5 mm if the 1.7 mm hooks are included. Note that the length change is due mostly to the buckling strip and the bent regions since the amount of foreshortening is minimized. These dimensions are provided by way of example as other dimensions are clearly contemplated by the present invention and use in different size vessels is also contemplated.

Figure 8:
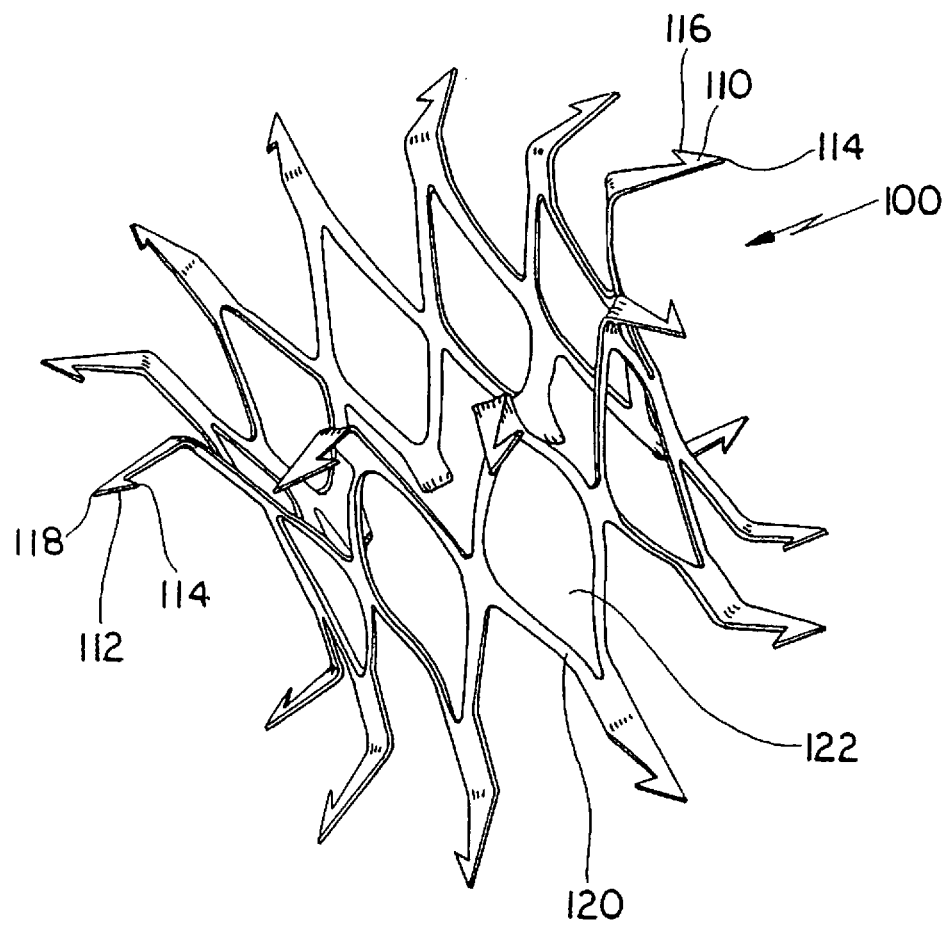
FIG. 8 is a perspective view of an alternate embodiment of the vascular device of the present invention shown in the expanded configuration.
Figure 11:
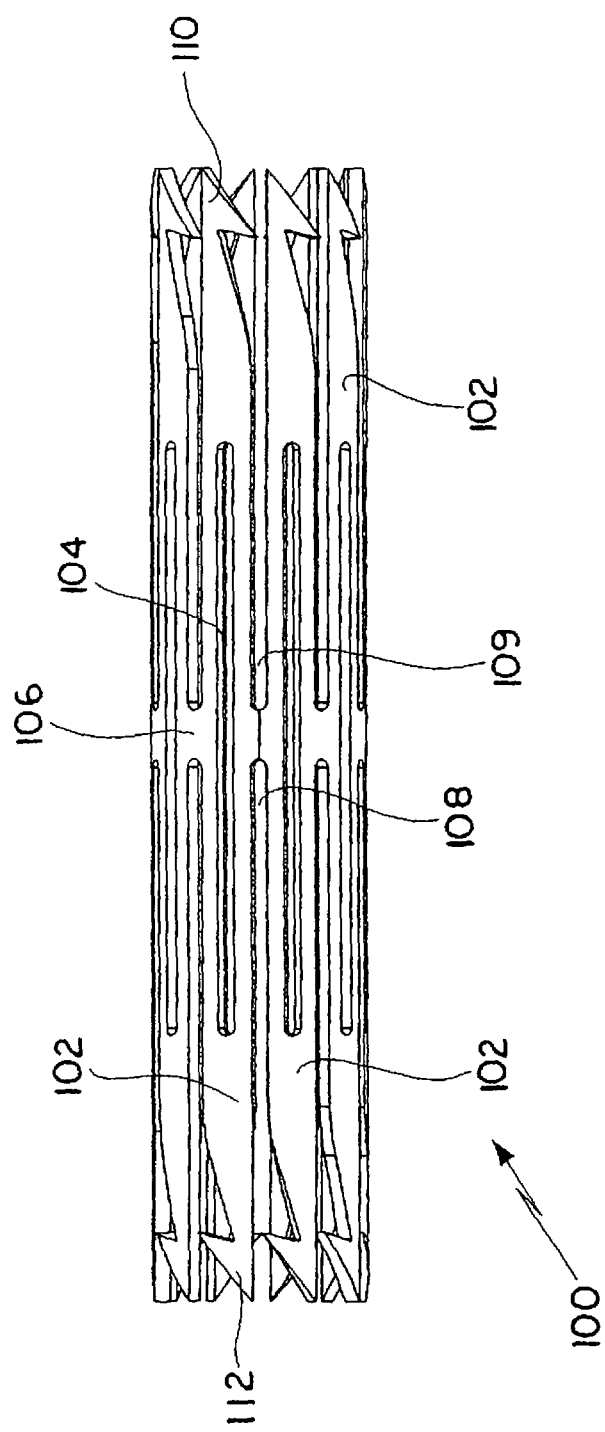
FIG. 11 is a side view of the vascular device of FIG. 8 in the collapsed configuration.

An alternate preferred embodiment of the vascular device of the present invention is shown in FIGS. 8-11, with FIGS. 8 and 9 showing the device in the expanded configuration and FIGS. 10-11 showing the collapsed configuration for delivery to the vessel.

Turning first to FIGS. 10 and 11, the device 100 is preferably laser cut from a cylindrical tube, forming a series, e.g. ten, of symmetrical longitudinal strips 102 terminating at opposite ends with vessel engaging members 110, 112. Each strip 102 has a longitudinal slot 104 formed therein having a uniform width throughout its length. Adjacent strips 102 are joined by transverse ribs or struts 106, creating a gap 108, 109 on either side of the ribs 106 between strips 102. Consequently, the device can be considered as forming one centrally located column of slots 104 with ribs 106 in axial alignment and slots 104 in axial alignment.

The vessel engaging members 110 and 112 are preferably in the form of hooks as described above in the first embodiment with each vessel engaging member 110 having a penetrating tip 114 and barb 116 and each member 112 having a penetrating tip 118 and barb 119. The penetrating tips 114 and 118 penetrate the vessel wall and prevent axial movement while the barbs 116, 119 restrict radial movement. In the collapsed configuration, as shown, the vessel engaging members 110, 112 are substantially parallel to the longitudinal axis of device 100, lying in the same plane as the respective longitudinal strip 102.

As shown, the cylindrical tubular member is formed into ten longitudinal strips 102 with ten hooks 110 at the proximal end 105 and ten hooks 112 at the distal end 107. Although ten longitudinal strips and ten vessel engaging members are shown on each end, it should be appreciated that fewer or greater number of longitudinal strips and vessel engaging members can be utilized. Moreover, not all of the longitudinal strips need to terminate in vessel engaging members, provided a sufficient number of strips have vessel engaging members to adequately secure the vessel.

The structure of the vascular device 100 is shown in its first expanded configuration in FIGS. 8 and 9. Vascular device 100, like device 10, is composed of a shape memory material, such as Nitinol, so that in its memorized configuration it assumes the shape shown in FIG. 8. The shape memory device is maintained in a collapsed configuration inside a sheath as described in more detail below, where it is cooled by a saline solution to maintain the device below its transition temperature. When the device 100 is delivered to the target site and released from the sheath, it is warmed by body temperature, thereby transitioning in response to this change in temperature to an austenitic expanded condition. Maintenance of the device in its softened martensitic state within the sheath facilitates delivery to the vessel as frictional contact between the device 100 and the internal walls of the delivery sheath would otherwise occur if the device was retained within the sheath in its austenitic condition.

When expanded, longitudinal slots 104 form substantially diamond shaped cells 120 with substantially diamond shaped openings 122. Upon expansion, the vessel engaging members 110 and 112 extend at an angle, preferably about 90 degrees, to the longitudinal axis of the vascular device 10 to enable the vessel engaging members 110 and 112 to engage and secure the vessel wall (see e.g. FIG. 9A). However, it is also contemplated that the vessel engaging members 110',112' could extend at a different angle, for example about 60 degrees, as shown in the alternative embodiment of FIG. 9B.

As the device moves from the collapsed configuration to the expanded configuration, it shortens in axial length as the diameter increases. For example, in one embodiment the length of the vascular device 100 in the collapsed configuration is about 1.8 cm and the diameter is about 3.5 mm. In the expanded configuration, the length decreases to about 1 cm, mainly due to the hooks bending up as foreshortening is minimized, and the diameter in the memorized expanded configuration increases to about 12 mm. (15.5. if the 1.75 mm hook length is included). These dimensions are provided by way of example as other dimensions are clearly contemplated.

Turning to the method of use of the vascular devices of the present invention, the insertion of vascular device 10 will be described, it being understood that vascular device 100 would be inserted in the same manner and expanded and retracted in the same manner as device 10.

Figure 12:
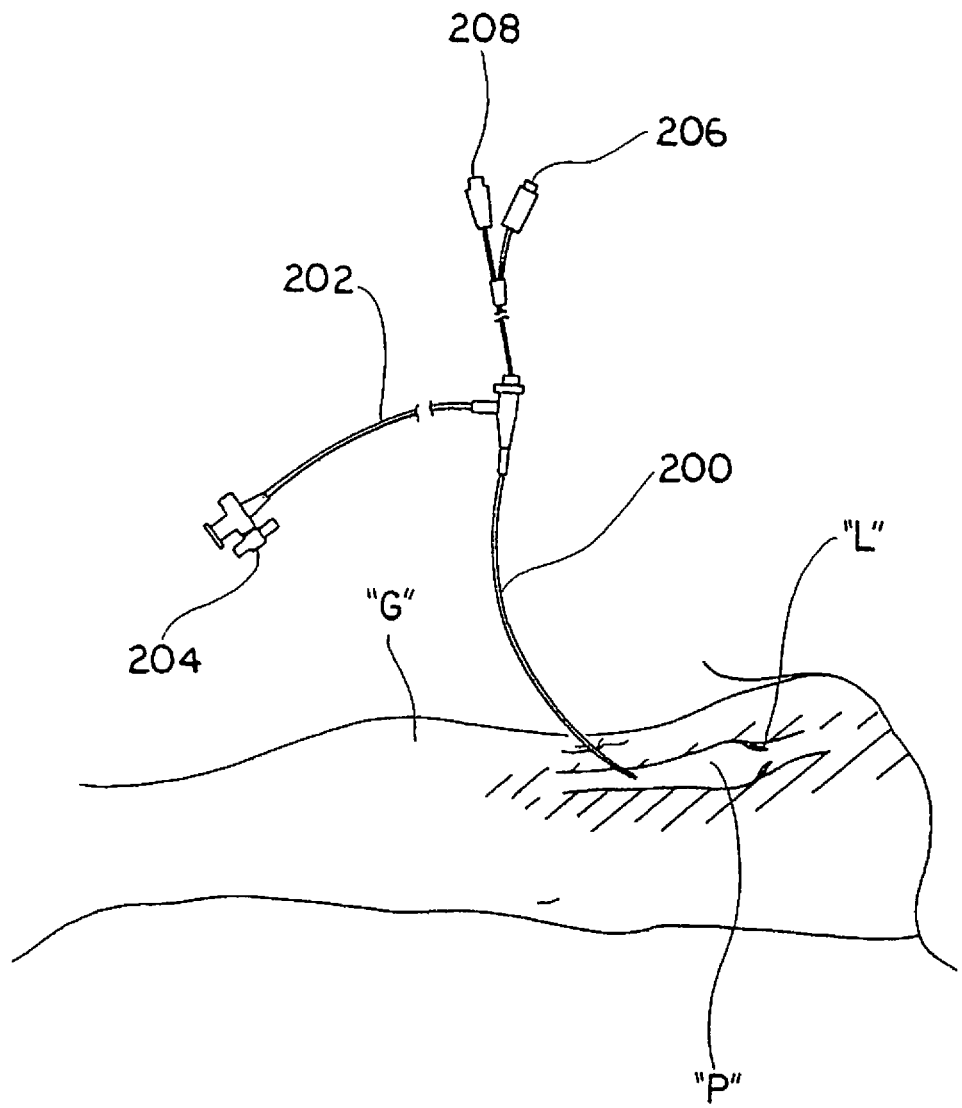
FIG. 12 illustrates one method of insertion of the vascular device of FIG. 1 showing the delivery catheter inserted directly into the popliteal vein in an antegrade direction.

There are several different methods of insertion of the vascular device of the present invention for treating venous valve insufficiency of the popliteal or saphenous vein. FIGS. 12-15 illustrate examples of some of these approaches by illustrating various access vessels for the delivery devices to reach these veins. In FIG. 12, the catheter 200 is placed into the popliteal vein "P" in the patient's leg "G" and advanced to a region adjacent the leaflets "T" to deploy the vascular device upstream of the leaflets. The delivery catheter is thus delivered in an antegrade fashion, with the tip extending downstream of leaflets "T" to deploy the device just upstream (defined in reference to the direction of blood flow) of the leaflets.

Figure 13:
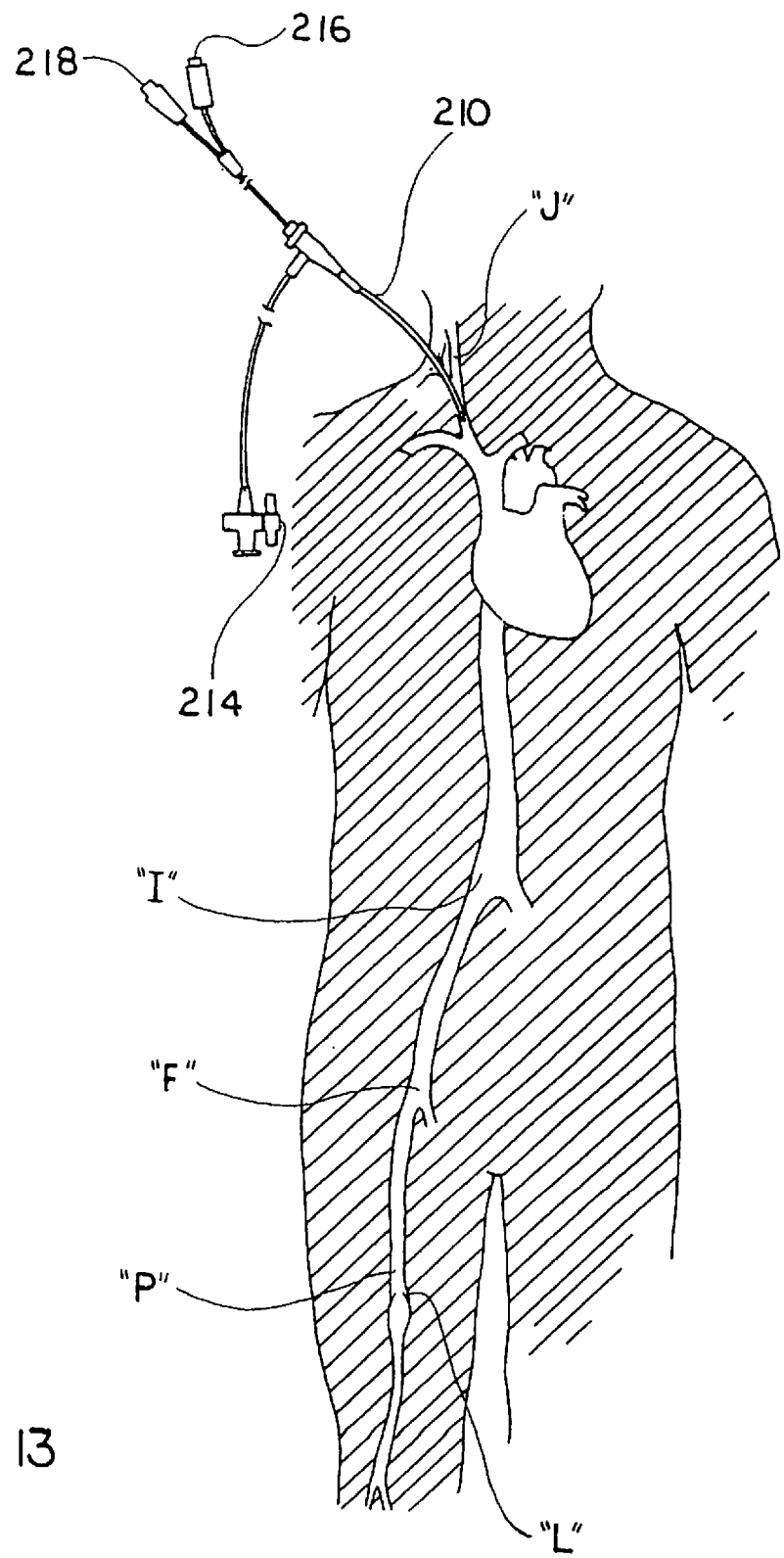
FIG. 13 illustrates an alternate method of insertion of the vascular device of FIG. 1 through the jugular vein for retrograde insertion into the popliteal vein.
Figure 14:
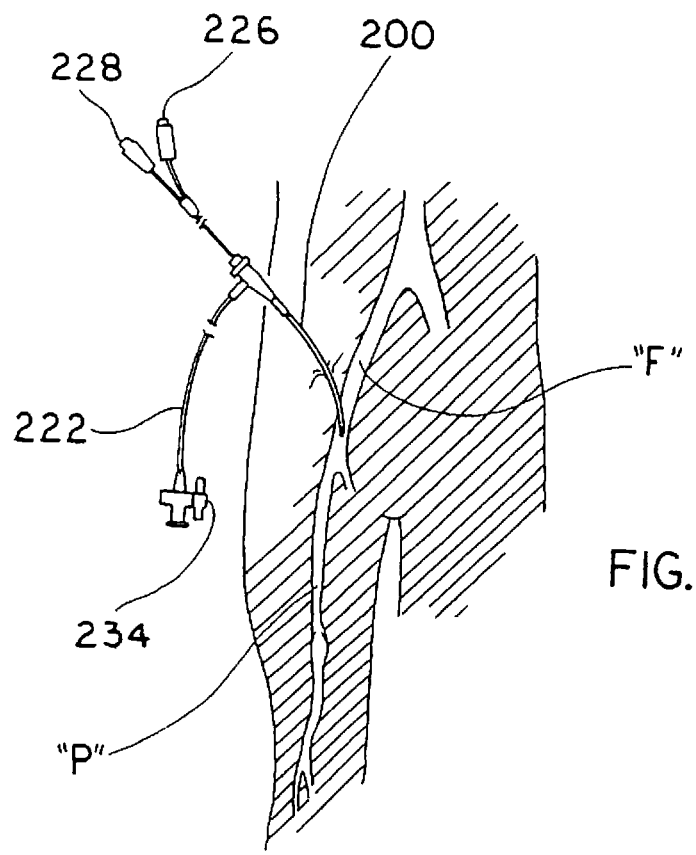
FIG. 14 illustrates another method of insertion of the vascular device of FIG. 1 showing the delivery catheter inserted through the right femoral vein for retrograde access to the popliteal vein.

In the approach of FIG. 13, the catheter 210 is inserted through the right jugular vein "J", where it will be advanced through the superior and inferior vena cava, past the iliac vein "I", through the femoral vein "F" and into the popliteal vein "P" through leaflets "L" in a retrograde fashion, i.e. opposite the direction of blood flow. The delivery catheter 210 would thus extend through the leaflet region just upstream of the leaflets. In FIG. 14, the catheter 220 is placed in the right femoral vein "F", where it will be advanced in a retrograde manner to the popliteal vein "P" in the manner described above with respect to FIG. 13.

Figure 15:
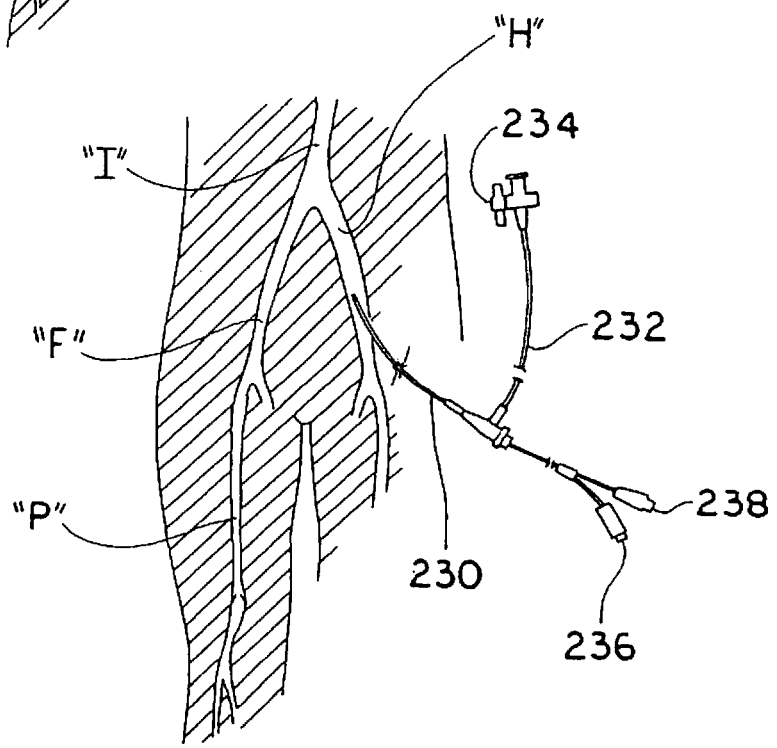
FIG. 15 illustrates yet another method of insertion of the vascular device of FIG. 1 showing a contralateral approach wherein the delivery catheter is inserted through the left femoral vein for advancement around the iliac vein for retrograde insertion into the right popliteal vein.

In the contralateral approach of FIG. 15, the catheter 230 is inserted through the left femoral vein "H" where it will be advanced around the iliac vein "I" and through the left femoral vein "F" into the popliteal vein "P."

Each of the delivery catheters 200, 210, 220 and 230 has respective tubing 202, 212, 222 and 232, with a stopcock 204, 214, 224 and 234 to control saline infusion through the catheter to maintain the vascular device 10 (or device 100) in the cooled martensitic collapsed configuration for delivery. Inflation port 206, 216, 226 and 236 provides for fluid infusion to inflate the balloon which is mounted on the catheter shaft and positioned within the device 10. The outer sheath of the delivery catheter slides with respect to the catheter shaft to expose the vascular device. Guidewire port 208, 218, 228 and 238 enables insertion of a conventional guidewire (not shown) to guide the delivery catheter intravascularly to the target site. A conventional access or introducer sheath (not shown) would be inserted through the skin and into the access vessel, and the respective delivery catheter would be inserted into the access vessel through the introducer sheath.

Figures 16, 17:
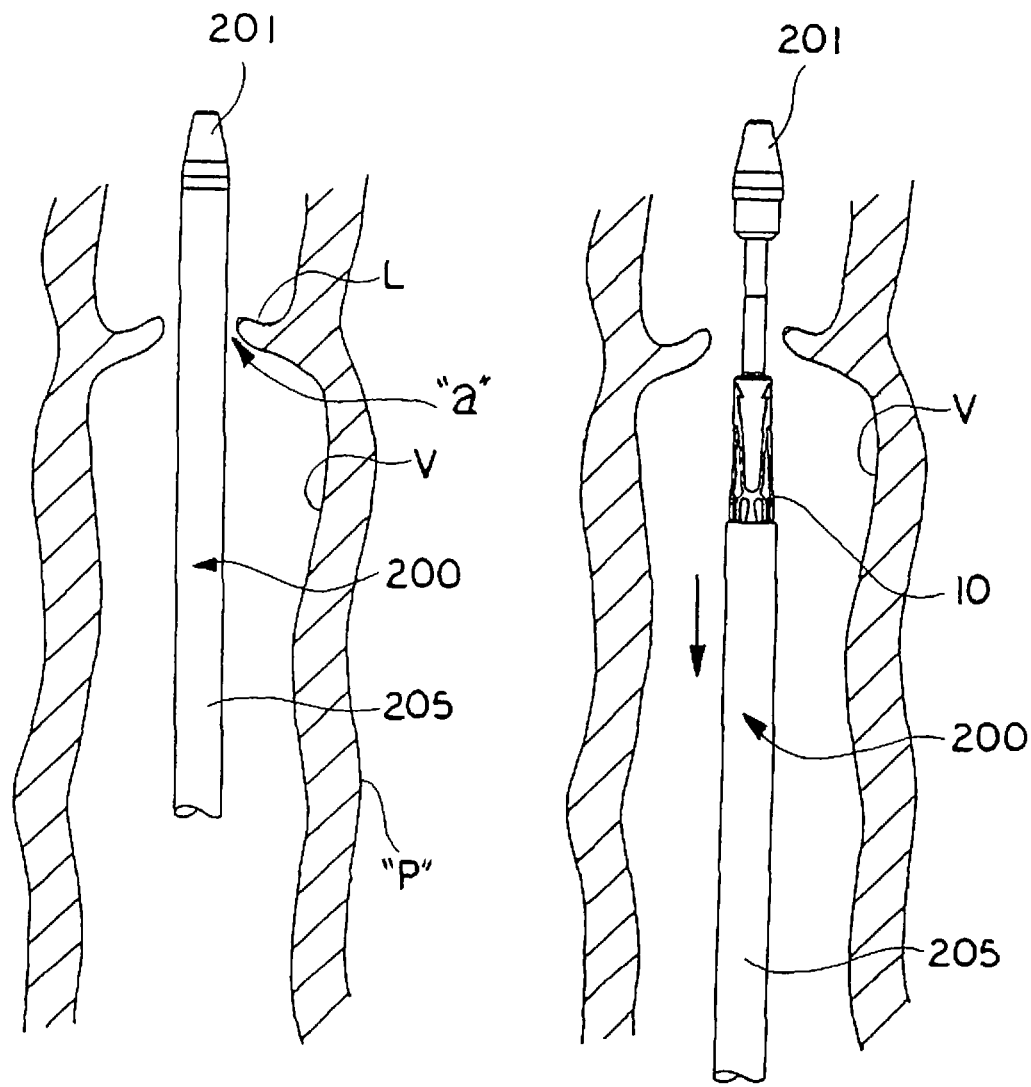
FIG. 16 shows a side view of the delivery catheter for the vascular device of FIG. 1, with the vessel wall shown in section, illustrating antegrade insertion of the delivery catheter in the popliteal vein.
FIG. 17 is a view similar to FIG. 16 showing initial withdrawal of the sheath in the direction of the arrow to partially expose the vascular device of FIG. 1.
Figure 18:
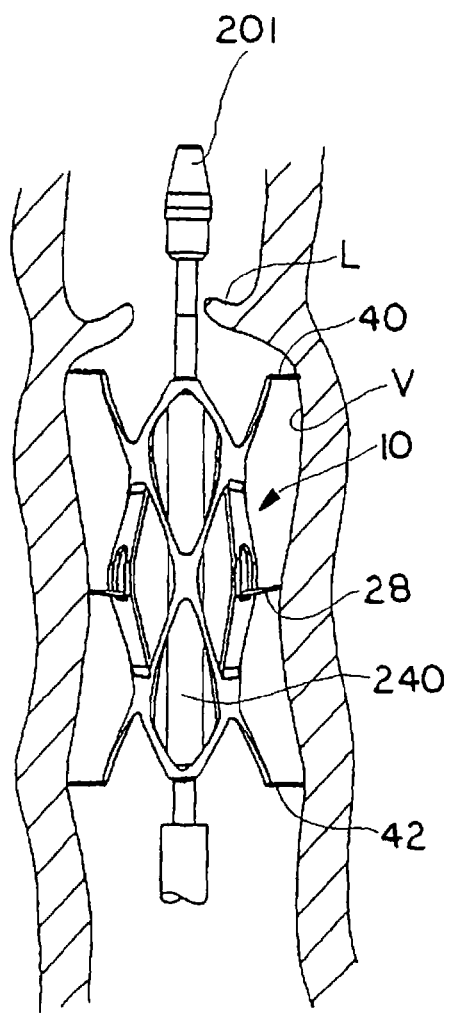
FIG. 18 is a view similar to FIG. 16 showing the vascular device of FIG. 1 expanded within the vessel, upstream (with respect to blood flow) of the valve leaflets, after the sheath has been fully withdrawn.

FIGS. 16-20 illustrate the method steps of insertion of the vascular device 10 in an antegrade fashion intravascularly in the popliteal vein "P". Catheter or delivery sheath 200 is inserted over a conventional guidewire (not shown) so the distal tip 201 of the catheter shaft extends past, i.e. downstream of the valve leaflets L extending annularly from vessel wall "V" as shown in FIG. 16. As can be appreciated, since there is a gap "a" between the valve leaflets "L", the valve cannot function properly because the leaflets cannot properly close to prevent backflow. Also, due to the malfunctioning of the valve, the vessel wall becomes dilated as shown as the weight and pressure of the backflow blood pushes out the vessel wall.

Once the position of the sheath 200 is confirmed by venography, intravascular ultrasound, or other means, the sheath 205 is withdrawn with respect to catheter tip 201 in the direction of the arrow of FIG. 17, exposing the vascular device 10. When the sheath 205 has been fully withdrawn to expose the device 10, the device is warmed by the body temperature and transitions to its austenitic phase and the first memorized expanded configuration of FIG. 18.

Figure 19:
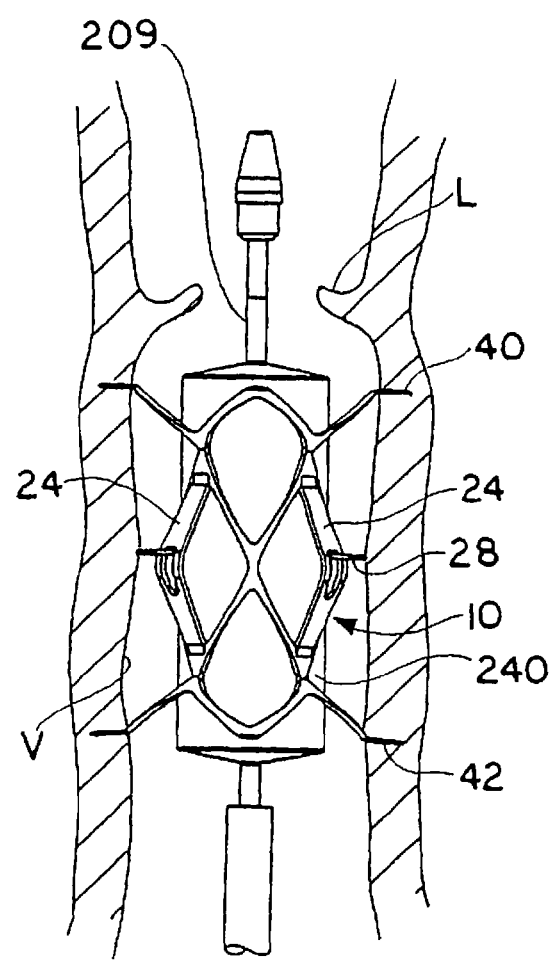
FIG. 19 is a view similar to FIG. 16, showing the vascular device of FIG. 1 expanded by a balloon so the vessel engaging members penetrate and retain the vessel wall.

Next, a balloon member 240 on catheter shaft 209 which is positioned within device 10 is inflated via introduction of fluid through inflation lumen 206 (FIG. 12) to further expand the device 10 to a second expanded configuration shown in FIG. 19. That is, the device is expanded to a larger diameter than the diameter in its memorized configuration of FIG. 18 so that vessel engaging members 28, 40 and 42 will engage the vessel wall "V" with the sharp tips and barbs penetrating the vessel wall to firmly grasp and secure it. This securement restricts both radial and axial movement of the vessel to enhance retention by the device 10.

After retention of the vessel wall as in FIG. 19, the balloon is deflated (and the catheter 200 removed), resulting in the device 10 contracting from the second expanded configuration towards its memorized configuration. Preferably, the device 10 will return to substantially the same diameter as the first (memorized) expanded configuration. As contracted, the device 10, due to the engagement of the vessel engaging members with the internal wall of the vessel, pulls the vessel wall radially inwardly, thereby pulling the leaflets radially inwardly to the position of FIG. 20 to close gap "a". As can be appreciated, the vessel wall is no longer dilated and the valve leaflets are sufficiently approximated such that their tips contact to block backflow and their function is therefore restored. The device 10 remains inside the vessel, maintaining the approximation of the vessel wall to maintain the proper functioning of the leaflets.

Figure 21A:
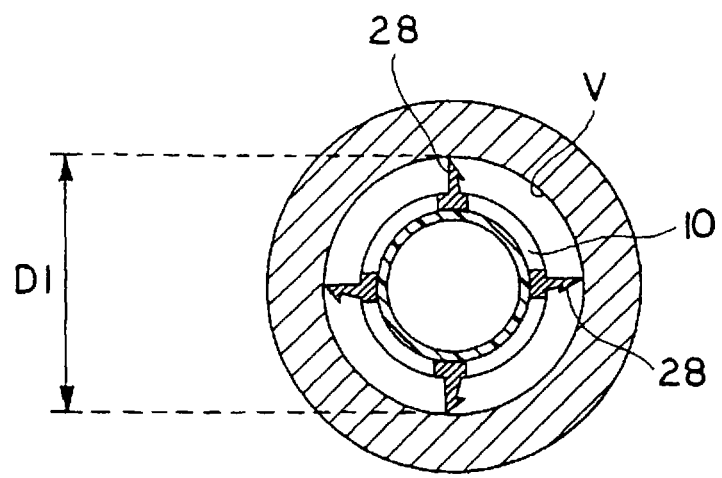
FIGS. 21A-21C are transverse cross-sectional views of the vascular device of FIG. 1 showing its interaction with the vessel wall during delivery and placement, wherein FIG. 21A corresponds to the initial position of the vascular device in FIG. 18 wherein the vessel engaging members have not penetrated the vessel wall (the balloon has been omitted for clarity)
Figure 21B:
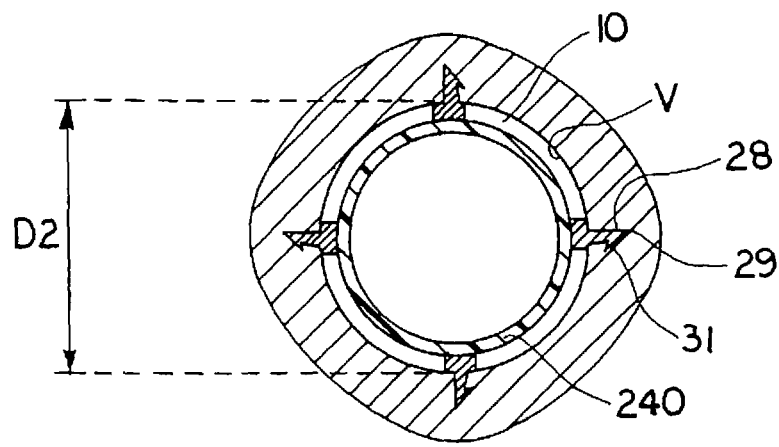
Figure 21C:
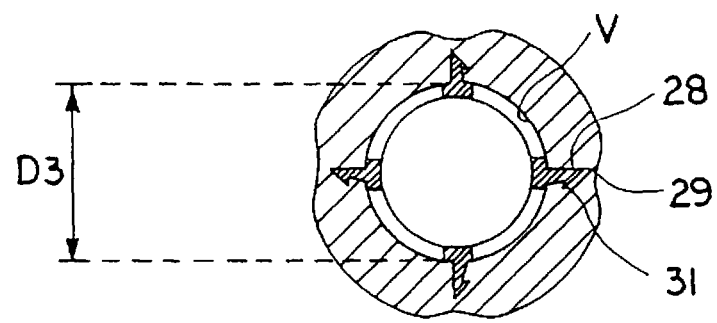
Figure 22:
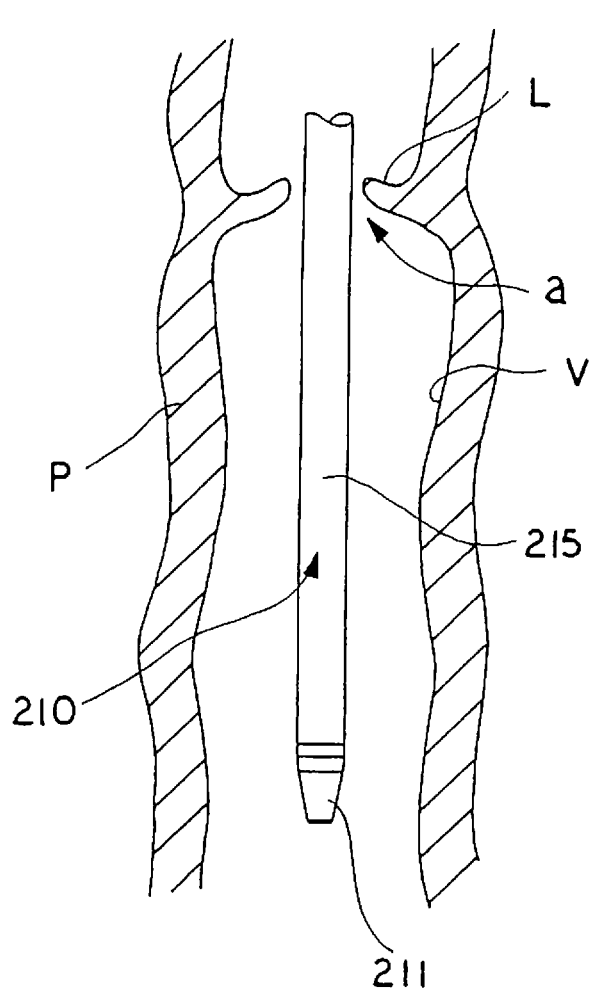
FIG. 22 shows a side view of the delivery device for the vascular device of FIG. 1, with the vessel wall shown in section, illustrating as an alternative, retrograde insertion of the delivery device in the popliteal vein.
Figure 23:
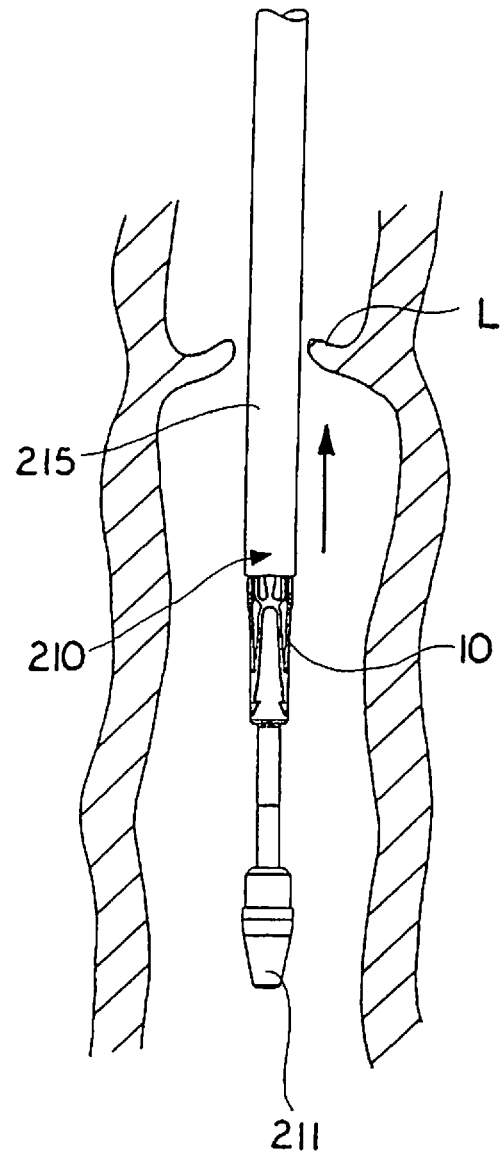
FIG. 23 is a view similar to FIG. 22 showing initial withdrawal of the sheath in the direction of the arrow to partially expose the vascular device of FIG. 1.
Figure 24:
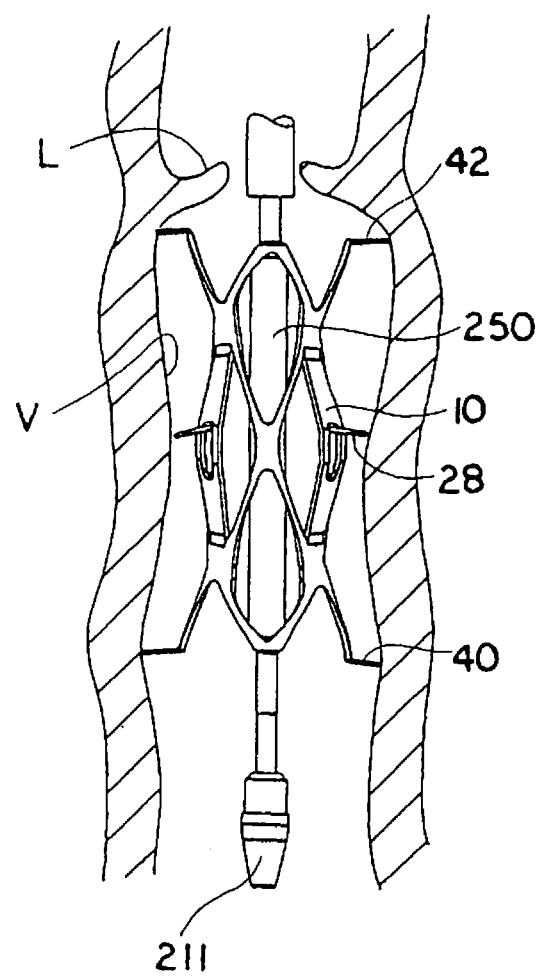
FIG. 24 is a view similar to FIG. 22 showing the vascular device of FIG. 1 expanded within the vessel, upstream of the valve leaflets, after the sheath has been fully withdrawn.
Figure 25:
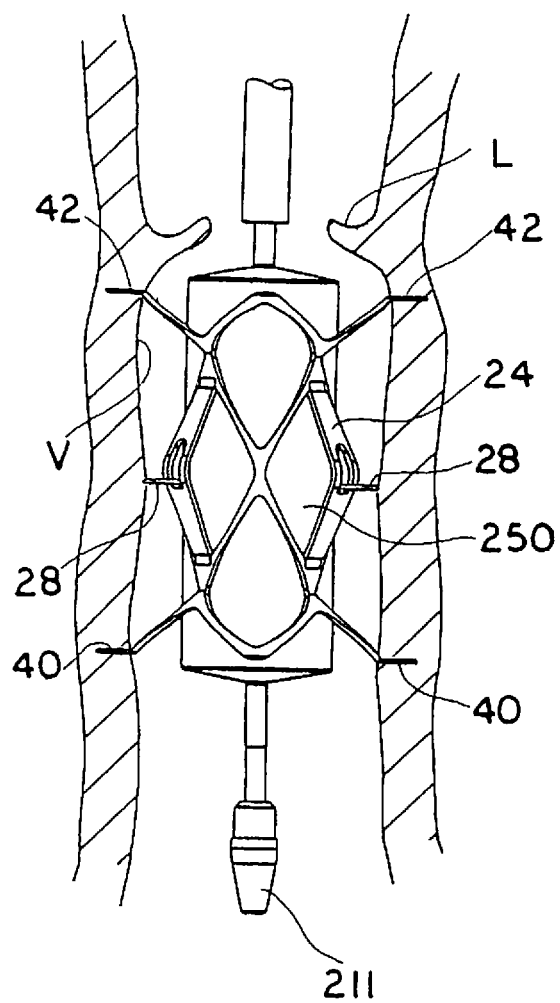
FIG. 25 is a view similar to FIG. 22, showing the vascular device of FIG. 1 expanded by a balloon so the vessel engaging members penetrate and retain the vessel wall.
Figure 26:
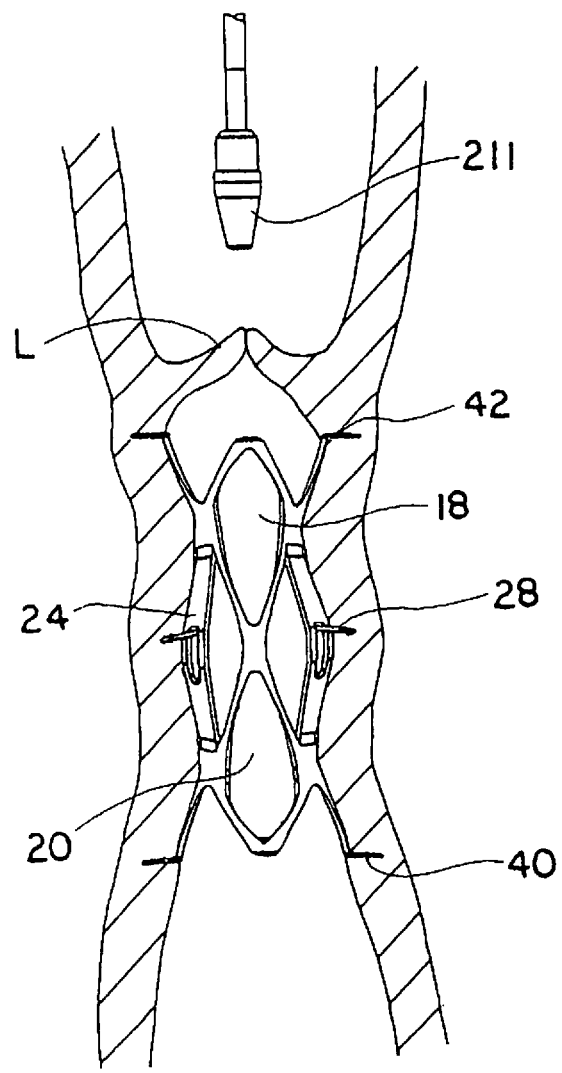
FIG. 26 is a view similar to FIG. 22, after the balloon is deflated and the catheter withdrawn from the vessel, showing the vascular device returned to its original position pulling the vessel wall together and bringing the valve leaflets into apposition.

The changing diameters of the vascular device 10 can also be appreciated by reference to the transverse cross-sectional views of FIG. 21A-21C. The delivery device has been removed for clarity. More specifically, FIG. 21A corresponds to the initial position of the vascular device 10 in FIG. 18 wherein the device 10 has been delivered to the target vessel, and has expanded to the first expanded (memorized) configuration but the vessel engaging members have not penetrated the vessel wall. It should be appreciated that in this configuration the vessel engaging members may or may not be in contact with the vessel wall, but in either case, do not fully penetrate and secure the vessel to the same extent as in the second position. As shown, by way of example, the unhealthy dilated vessel can have an internal diameter D1 of approximately 14 mm. The balloon is not shown in FIG. 21A for clarity.

FIG. 21B corresponds to the position of the vascular device in FIG. 19 wherein the balloon has been inflated to radially expand the device 10 to a second expanded position to enable the vessel engaging members to penetrate and retain (secure) the vessel wall. In this configuration, the vessel wall is further expanded to a diameter D2 of about 16 mm, as the device is expanded to a diameter of about 16 mm, with the hooks extending an additional 2 mm so the device is expanded to 20 mm.

Figure 20:
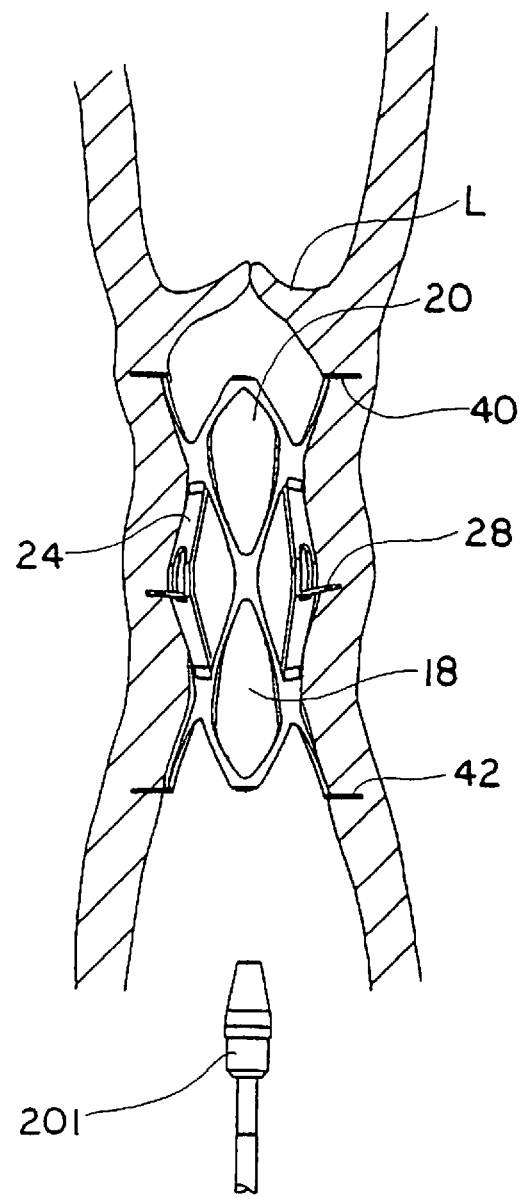
FIG. 20 is a view similar to FIG. 16, after the balloon is deflated and the catheter withdrawn from the vessel, showing the vascular device returned to its original position pulling the vessel wall together and bringing the valve leaflets into apposition.

FIG. 21C corresponds to the position of the vascular device 10 in FIG. 20 wherein the balloon has been deflated and the device contracted to bring the vessel wall radially inwardly. The internal vessel wall diameter will preferably be about 12mm to close the gap between the leaflets. The diameter of the vascular device 10 preferably returns to the same diameter as in FIG. 21A, e.g. about 12 mm. As can be seen the device 10 abuts the vessel wall V.

FIGS. 22-26 illustrate retrograde insertion of the vascular device 10. In this approach the delivery catheter, e.g. catheter 210, is inserted in a direction against the blood flow so tip 211 extends past the valve leaflets "L" in the popliteal vein "P" and the catheter 210 is positioned so the device 10 will be deployed upstream of the leaflets. The deployment of the device 10 is otherwise the same as in FIGS. 16-20. That is, sheath 215 of the delivery device 210 is retracted in the direction of the arrow of FIG. 23, to expose the device 10. Full retraction and removal of the sheath 215 to expose the device to the warmer body temperature enables it to expand to its memorized (first expanded) configuration of FIG. 24. Subsequent expansion of balloon 250 (FIG. 25) causes the vessel engaging members 42, 28, 40 to penetrate and retain the vessel wall so that upon deflation of the balloon, the device 10 returns to the memorized configuration of FIG. 26 pulling the vessel wall inwardly and bringing the valve leaflets "L" closer together into apposition so the tips can contact. The changing diameters would also correspond to the aforedescribed transverse cross-sections of FIG. 21A-21C.

As can be appreciated, device 10 and device 100 are each symmetrical so that the "proximal" and "distal" portions are identified herein for convenience.

Figures 27, 28, 29:
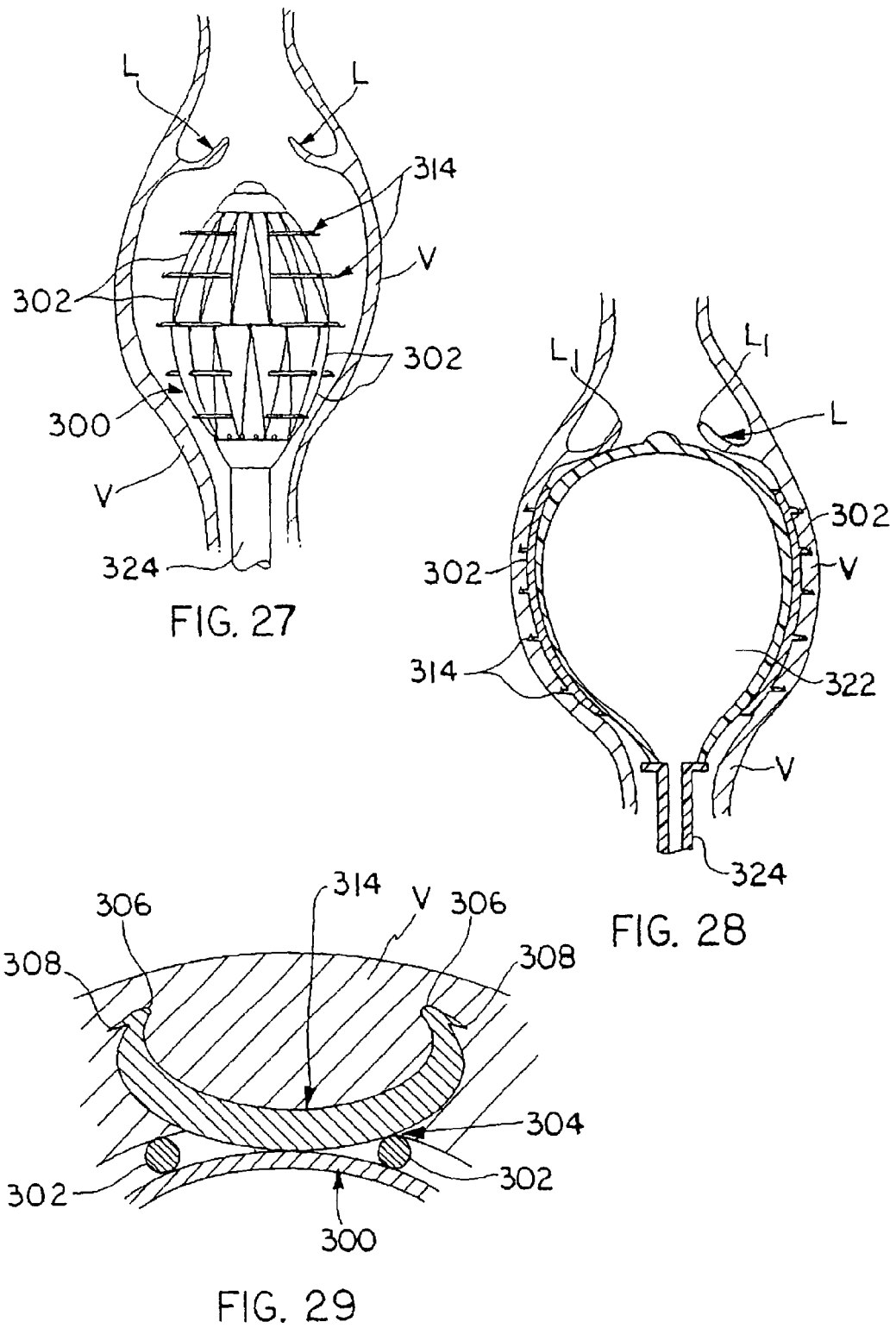
FIG. 27 is a side view of an alternative embodiment of the vascular device in the expanded position shown within a vessel (the vessel wall is shown in section)
FIG. 28 is a view similar to FIG. 27 showing a balloon expanding the vascular device so the hooks penetrate the vessel wall.
FIG. 29 is an enlarged view of the hook of the device of FIG. 27 embedded in the vessel wall.

FIGS. 27-29 illustrate an alternate embodiment of the vascular device designated generally by reference numeral 300. This shape memory device 300 is illustrated and described in Provisional patent application No. 60/214,120, filed Jun. 6, 2000, the entire contents of which are incorporated herein by reference. Device 300 is placed within vessel V, e.g. the popliteal vein, to approximate leaflets "L" which as shown in FIG. 27 are not functioning properly because the tips L1 are spaced apart. In its first expanded configuration corresponding to its memorized shape of FIG. 27, hooks 314 have not penetrated the vessel wall. The device 300 is formed by struts 302 as described in detail in the '120 application. Hooks 314, affixed to struts 302 at region 304 are crescent shaped and have pointed ends 306 with barbed portions 308.

In the expanded configuration of FIG. 28, balloon 322 on shaft 324 of the delivery device has expanded the device 300 so that hooks 314 penetrate and securely engage the vessel wall "V". The balloon would then be deflated and the device 300 would return to its first expanded configuration bringing the vessel walls radially inwardly and bringing the valve leaflets into apposition in the same manner as described above with respect to vascular device 10.

Figure 30:
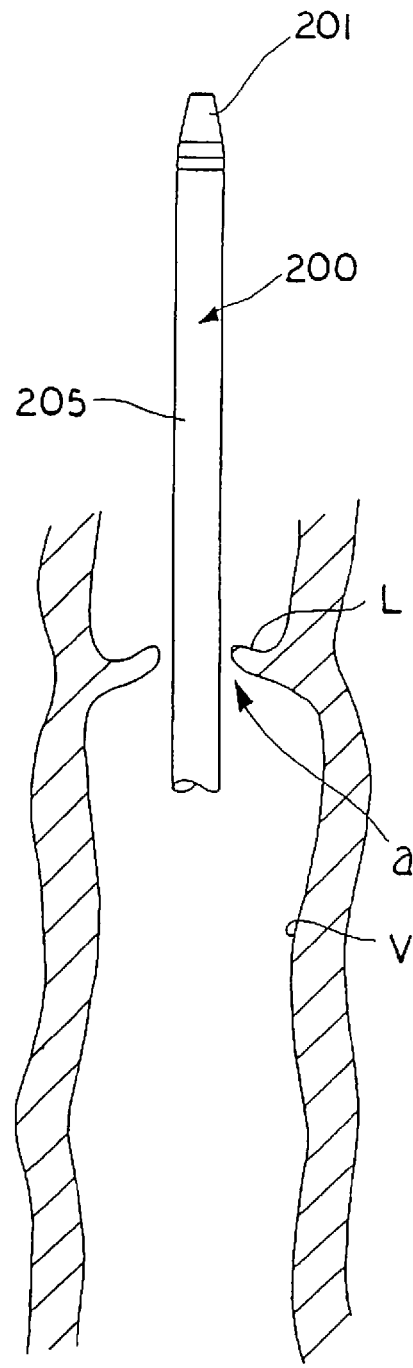
FIG. 30 shows a side view of the delivery catheter for the vascular device of FIG. 1, with the vessel wall shown in section, illustrating as another alternative, antegrade insertion of the delivery catheter in the popliteal vein for positioning of the vascular device downstream of the valve leaflets.
Figure 31:
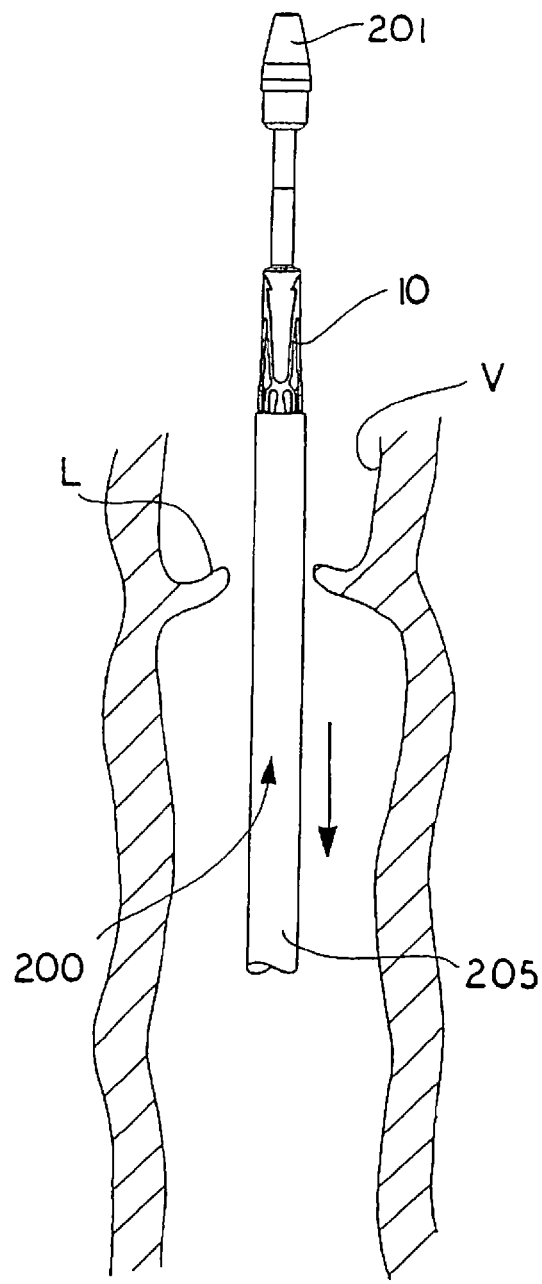
FIG. 31 is a view similar to FIG. 30 showing initial withdrawal of the sheath in the direction of the arrow to partially expose the vascular device of FIG. 1.

FIGS. 30 and 31 illustrate an alternate method of placement of the vascular device. In this method, the vascular device 10 (or vascular device 100) is placed downstream (with respect to the direction of blood flow) of the valve leaflets. The delivery catheter 210' is inserted in the same antegrade manner as described above with respect to FIG. 16, except it is advanced sufficiently past the valve leaflets L to enable downstream delivery of the device 10. Once positioned as shown in FIG. 31, the sheath 215' is withdrawn in the direction of the arrow, enabling the device 10 to expand to its memorized configuration. Vascular device 10 would then be further expanded by a balloon and then enabled to contract to its memorized configuration in the same manner as in FIGS. 18-20, the only difference being that the device 10 would grasp the vessel wall downstream of the valve leaflets to pull the vessel wall radially inwardly to bring the leaflets into apposition.

It should be appreciated that the device 10 or device 100 could also be delivered in a retrograde fashion such as shown in FIGS. 13-15 for positioning of the device downstream of the leaflets L.

FIGS. 32-34 illustrate an alternative delivery system and method for vascular device 10 (or device 100 which can be delivered in the same manner). In this method, exposure of the vascular device to body temperature and expansion of the balloon occur substantially simultaneously. To facilitate placement, a restraint system for connecting the vascular device to the balloon is provided.

More specifically, balloon 250' has a pair of sutures 252 attached thereto at a proximal and distal portion which wrap around the vascular device 10 forming a loop of suture to connect the balloon and the device. Although two sutures, are shown, it is contemplated that one suture or more than two sutures can be utilized to connect the balloon 250' to the vascular device 10. Additionally, other restraint systems such as perforated strips can be utilized.

In the position of FIG. 32, the sutures (only one of which is shown, the other suture still within the sheath 215') are loosely wrapped around the device. As the sheath 215' is retracted in the direction of the arrow, the balloon is inflated. Thus, as the sheath 215' is fully withdrawn, the device expands to the position of FIG. 33, without the intermediate step required in the methods described above, i.e. without the step of FIG. 24 which first allows the device to expand to the memorized configuration. As the balloon expands, the pressure against the sutures 252 breaks the suture loops, thereby releasing them from the vascular device 10. This way, when the balloon 250' is deflated and withdrawn with the delivery catheter 210' from the body, the sutures 252 are removed as well. Upon deflation, the vascular device 10 returns to its memorized configuration to pull the vessel wall radially inwardly in the manner described above to assume a position like that of FIG. 26.

Note that it is also contemplated that the balloon 250' can be inflated first within the sheath, followed by withdrawal of the sheath to expose the vascular device 10 to body temperature.

Additionally, the restraint system can also be utilized with the sequential method of deployment of FIGS. 16-20 and FIGS. 22-26. The restraint system, e.g. the sutures, would help prevent axial movement and help center the balloon with respect to the vascular device 10. Other restraint systems, such as a strap, could be used to releasably connect the vascular device to the balloon.

As an alternative to shape memory, a stainless steel or polymeric vascular device. Such device would be expanded by a balloon below its elastic limit, thus enabling the device to return to its smaller configuration after the balloon is deflated. The vascular device could also be in the form of a braided structure which can be expanded to engage the vessel wall by squeezing or compressing its end(s), and then releasing it to enable it to return to its more elongated position of reduced diameter to approximate the vessel wall.

Vascular Device with Replacement Valve

The foregoing embodiments of FIGS. 1-34 describe and show vascular devices which bring the vessel wall radially inwardly to approximate the patient's existing valve leaflets of the patient. In another aspect of the present invention, instead of approximating the valve leaflets, the vascular device inserted in the vessel has a replacement valve attached thereto. Thus, the vascular device is inserted to expand and contract as described above, bringing the dilated vessel wall radially inwardly and leaving the replacement valve inside the vessel attached to the implanted vascular device. This replacement valve can be utilized as a total replacement wherein the patient's valve leaflets are removed, or can be placed upstream or downstream of the patient's leaflets, leaving the nonfunctioning leaflets in place. Various embodiments of valve configurations used in conjunction with vascular devices are described in detail below and illustrated in FIGS. 38-48. FIGS. 38-48, for simplicity, show the vascular device schematically, it being understood that any of the foregoing vascular devices can be utilized with the various valve configurations. The valves can be attached at the proximal end, distal end, or intermediate the proximal and distal ends of the vascular devices.

Figure 9A:
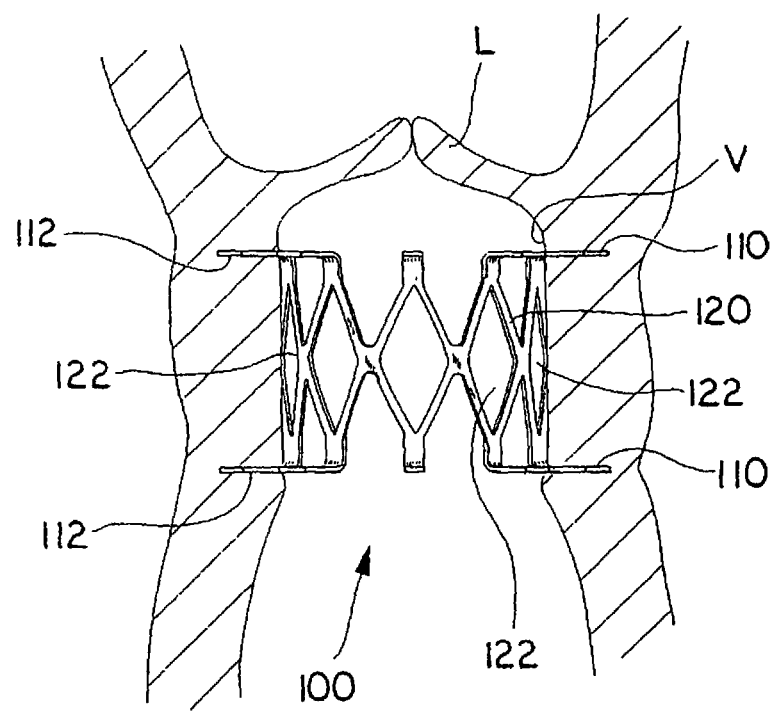
FIG. 9A is a side view of the vascular device of FIG. 8 shown in the expanded configuration.
Figure 9B:
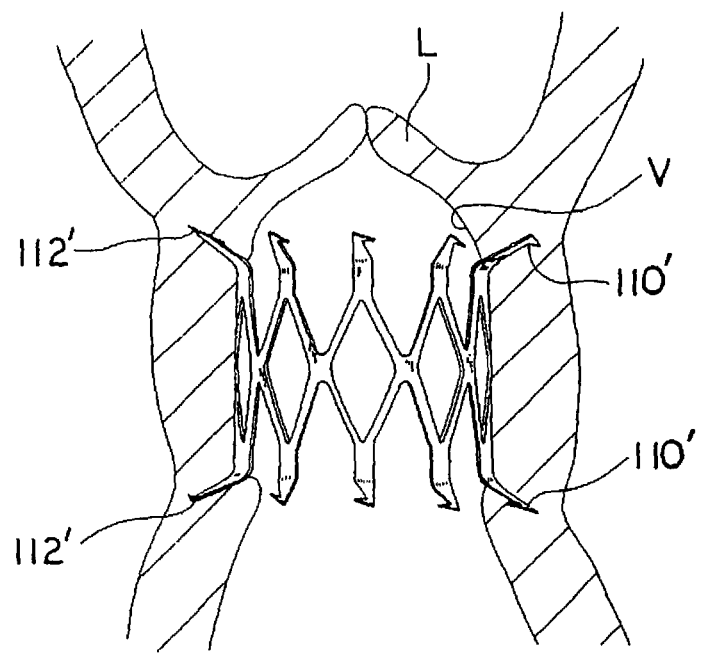
FIG. 9B is a side view similar to FIG. 9A except showing an alternate embodiment where the vessel engaging members extend at an angle into the vessel wall.

Turning first to FIGS. 35A-37, vascular device 400 is substantially identical to vascular device 100 of FIG. 9A, except for the provision of valve 450. For this reason, it has been labeled with a different reference numeral. Valve 450 is conically shaped and is secured to vascular device 400 by various techniques such as by being molded onto the frame or sewn onto the frame. A pair of elongated supports 455 extends from the device into the valve 450 which spread to close the valve and move inwardly to open the valve. The valve 450 is shown attached to the distal end to extend downstream of the device 400, with respect to blood flow. The valve 450 is shown in the open position in the figures and would collapse to a closed position by spreading of the supports 455, operating like a duckbill valve.

As an alternative, the supports 455 are not provided and the valve 450 functions in a similar manner described below with respect to the other conical valves, e.g. valve 500.

Figure 35B:
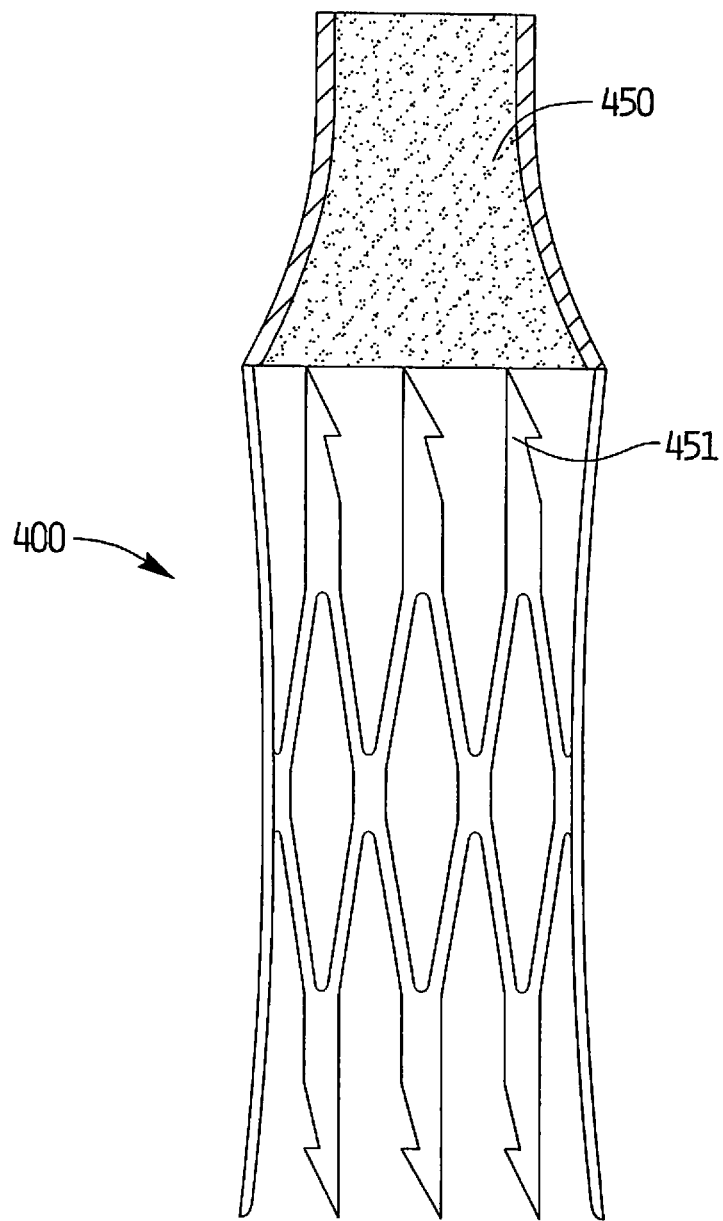
FIG. 35B is a side view of the vascular device of FIG. 35A in the collapsed position.
Figure 36A:
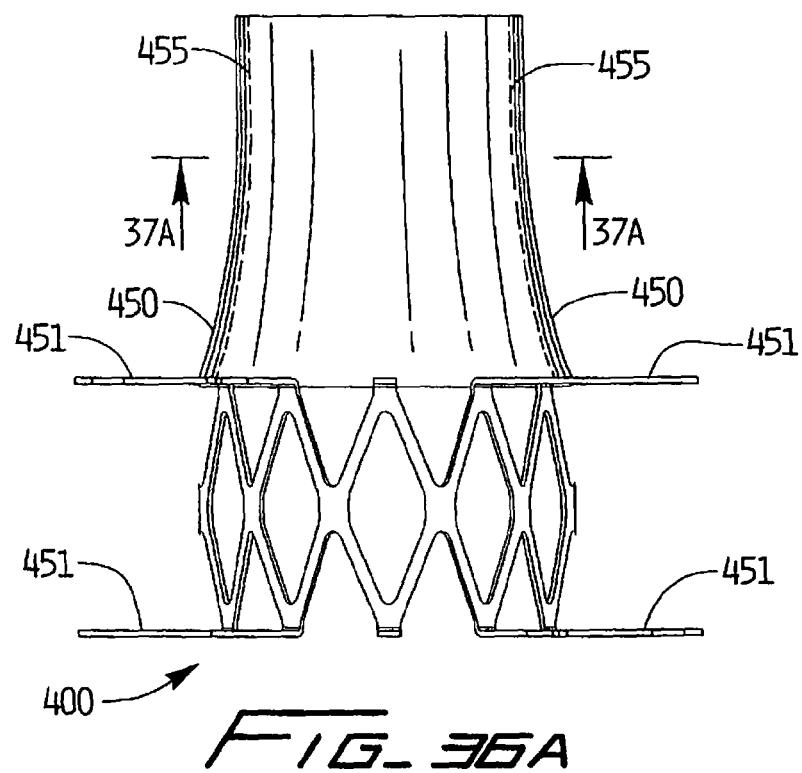
FIG. 36A is a side view of the vascular device of FIG. 35A shown in the expanded position.
Figure 37A:
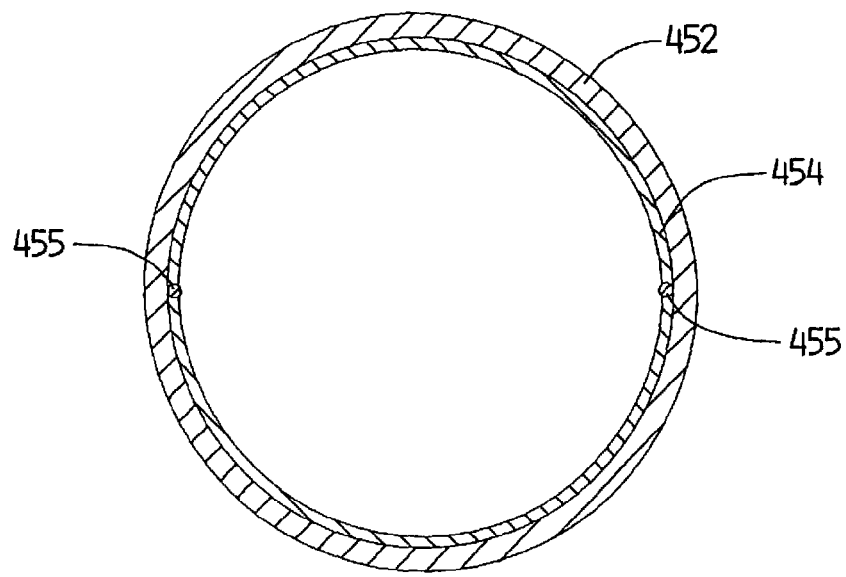
FIG. 37A is a transverse cross-sectional view of the vascular device of FIG. 36A.

A reinforcement ring as described below could also optionally be provided. Valve 450 can be multi-layered, with an outer layer 452 composed of one material and an inner layer 454 composed of another material as shown in FIG. 37A. Possible valve materials are discussed below It should be appreciated that the vessel engaging members 451 can extend substantially perpendicular as shown in FIG. 36A, or can extend at an angle as described above with respect to FIG. 9B. (See vessel engaging members 451' of FIG. 36B). Also, although the vessel engaging members of FIG. 35A are slightly longer and are bent at a different region than the device of FIG. 9A, it should be understood that the device of FIG. 9A can be provided with valve 450 or any of the other valve configurations described herein.

Turning now to FIGS. 38-47, the vascular device, since it is shown schematically for ease of reference, will be referred to in each of the drawings by reference letter "D", it being understood that preferably vascular device 100 is utilized, although device 10 and other support structures could alternatively be used.

With reference first to FIGS. 38A and 38B, valve 500 is conical in shape and has an open proximal end 504 and an open distal end 502. This conical shape results in backflow of blood causing the valve to close. When the valve 500 is in the position of FIG. 38A, distal opening faces towards and can press against the vessel wall to prevent flow through the valve 500. The force of the blood during systole straightens the distal end 502 to the position of FIG. 38B to allow blood flow therethrough. Reinforcement ring 506 helps to maintain the valve 500 in the open position. As shown, valve 500 extends distally of the device D so it is positioned downstream with respect to blood flow of the device.

FIGS. 39A and 39B illustrate a variation to the valve configuration of FIG. 38 in that it is similar to valve 500 except that the valve 520 is attached to a proximal end E of the vascular device D. Valve 520 is attached at points E1, E2, etc. around the circumference and extends upwardly through a central portion of the device "D". Reinforcement ring 526 functions to help maintain the valve 520 in the open position of FIG. 39B. FIG. 39A shows the valve 520 in the closed position and FIG. 39B illustrates the valve in the open position to enable blood flow therethrough. In both positions, the valve extends within vascular device D.

Figure 40A:
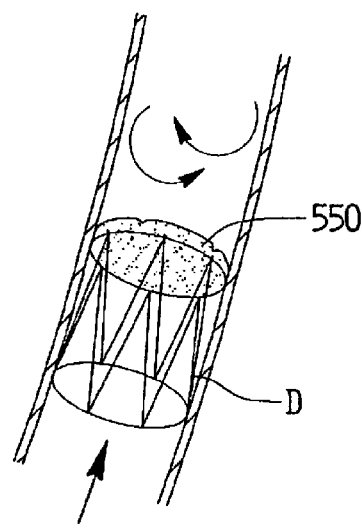
FIG. 40A is a perspective view of a fourth embodiment of the replacement valve of the present invention shown in the closed position to prevent blood flow therethrough, the vascular device being shown schematically.
Figure 40B:
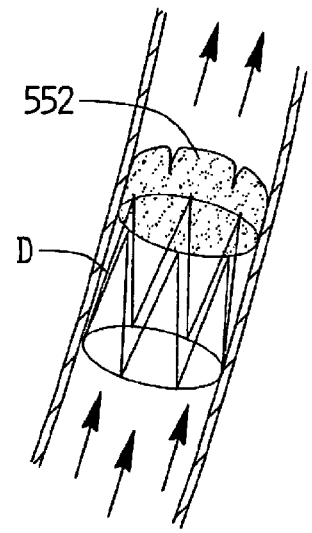
FIG. 40B is perspective view showing the valve of FIG. 40A in the open position to enable blood flow.

In the embodiment of FIG. 40, the valve 550 is attached to the distal end of vascular device D and has a plurality of leaflets or petals 552 arranged circumferentially thereabout. The leaflets fold inwardly towards each other in the closed position of FIG. 40A to prevent blood flow. The pressure of the blood during systole forces the leaflets apart to the open position as shown in FIG. 40B.

Figure 41A:
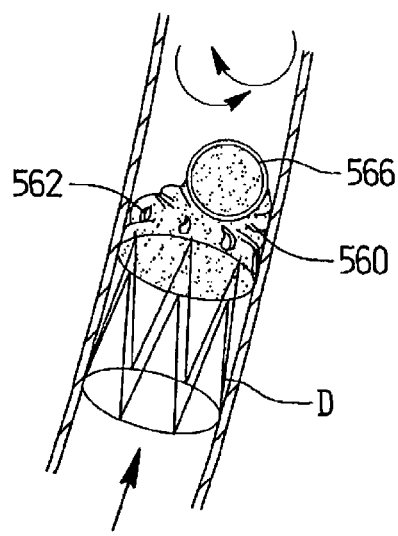
FIG. 41A is a perspective view of a fifth embodiment of the replacement valve of the present invention having drainage slits formed therein and shown in the closed position to prevent blood flow therethrough, the vascular device being shown schematically.
Figure 41B:
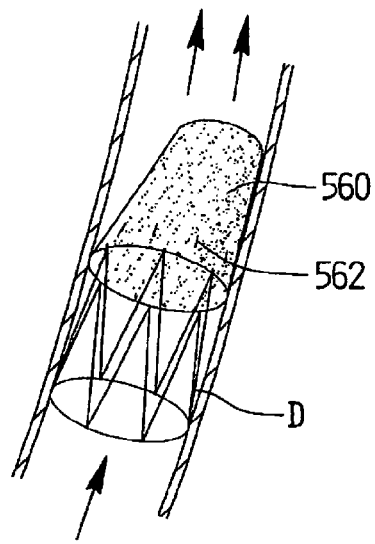
FIG. 41B is perspective view showing the valve of FIG. 41A in the open position to enable blood flow.

In the embodiment of FIGS. 41A and 41B, valve 560 is conically shaped like the valves of FIGS. 38 and 39, but is offset from the central longitudinal axis of vascular device D. Additionally, eccentric valve 560 differs from valves 500 and 520 in that it has a plurality of slits 562 at a proximal portion to enable drainage of blood to reduce blood buildup. That is during the diastole phase, the slits expand to larger holes as shown in FIG. 41A and the blood draws through the holes. Reinforcement ring 566 functions as described above to help retain the distal end open.

A duckbill valve 570 is illustrated in the embodiment of FIGS. 42-44. Valve 570 is attached at the distal end of vascular device D and is moved to the open position as shown in FIG. 43 by blood flow to enable passage therethrough. The closed position of the valve is illustrated in FIGS. 42 and 44. The proximal region of valve 570 is slightly tapered. As with any of the foregoing valves, valve 570 can be attached at the proximal end, distal end, or intermediate portion of the vascular device.

FIGS. 45-47 illustrate steps for placement of the vascular device of the present invention. FIG. 45 shows placement in the popliteal vein "P" and the femoral vein "F" of the vascular device of FIG. 41 by way of example, it being understood that any of the vascular devices with any of the valve configurations can be placed in a similar fashion. Placement of two vascular devices is shown, although only one vascular device D (shown schematically) or more than two can be utilized. In FIG. 46A, the vascular device and valve 560 are introduced through introducer sheath 600 in a collapsed position. The device is retained within a delivery catheter 604. After introduction of the catheter 604 through the introducer sheath 600 to the surgical site, the pusher 606 pushes the device to the end of the catheter 604, is then retracted, followed by retraction of the catheter 604, thereby releasing the device and allowing it to expand to the memorized configuration as shown in FIG. 46C for retention in the vein. Alternatively, the pusher can be used to fully advance the device from the catheter 604.

Figure 47A:
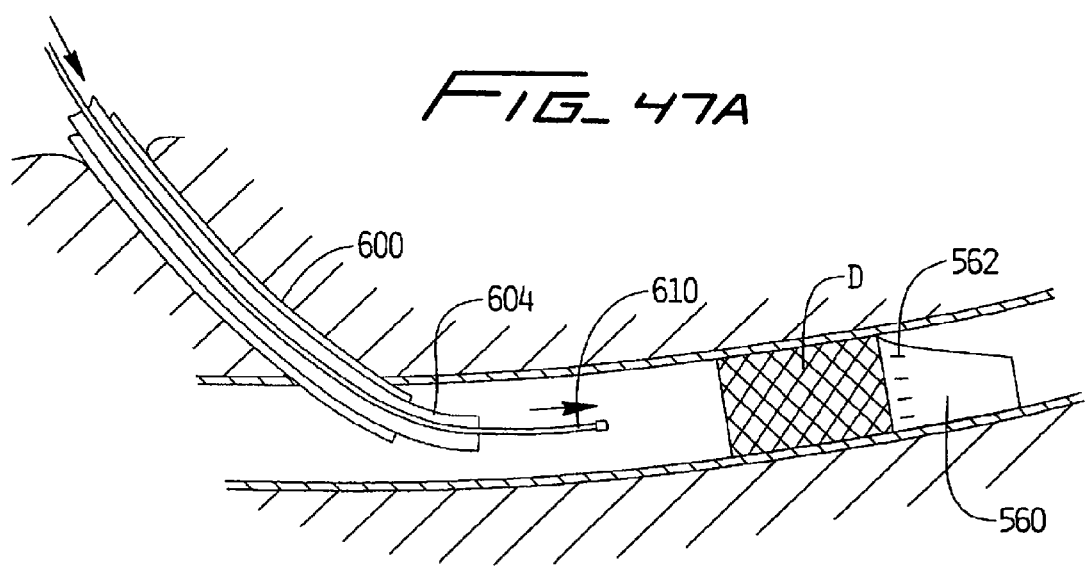
Figure 47B:
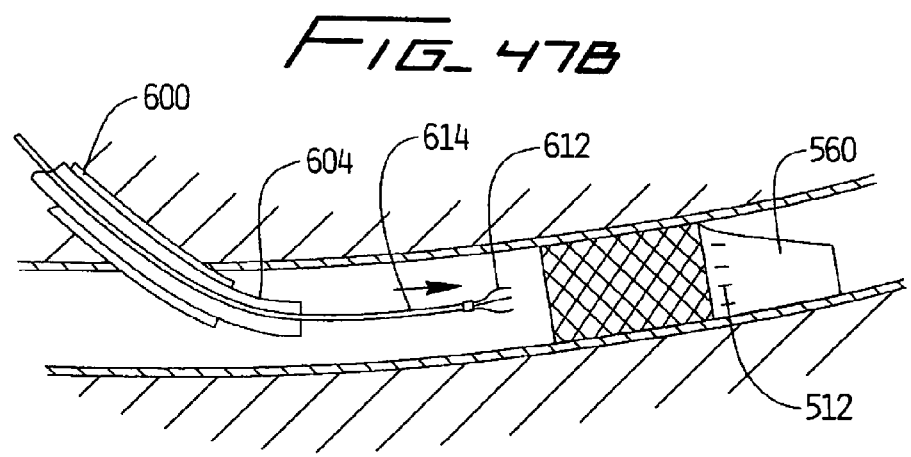
Figure 47C:
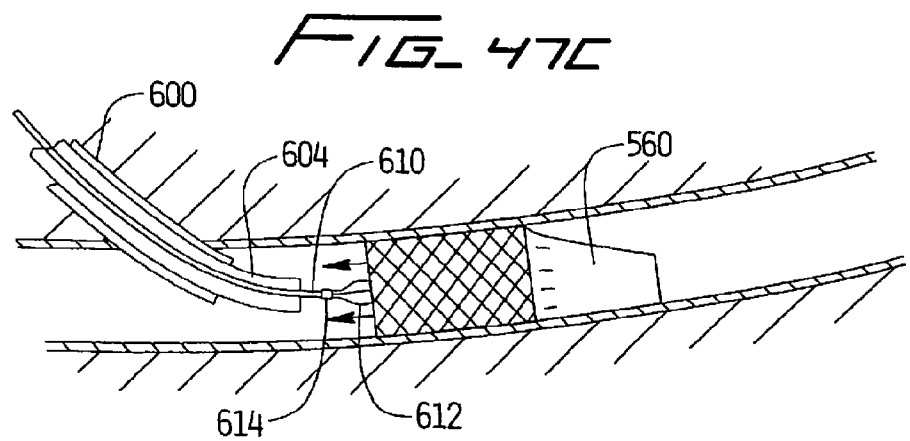

If it is desired to reposition the device, grasper 610 within delivery catheter 604 is inserted through the introducer sheath 602. The prongs or fingers 612 are advanced from the outer tube 614 of grasper 610, or the outer tube 614 is moved proximally, to expose the prongs 612. The outer tube 614 is then advanced slightly to slightly clinch the prongs 612 so the prongs 612 can grasp the vascular device D and pull it to a more proximal position as shown in FIG. 47C. The grasper 610 is then removed. Note valve 560 is shown in the open position in FIGS. 47A-47C.

Figure 48A:
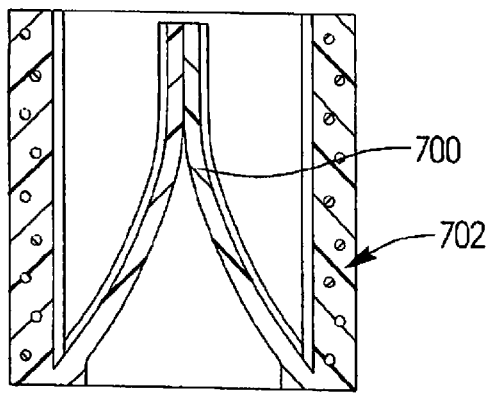
FIG. 48A is a cross-sectional view of a seventh embodiment of the replacement valve of the present invention having a reinforcement therein, and shown positioned with a covered stent.
Figure 49A:
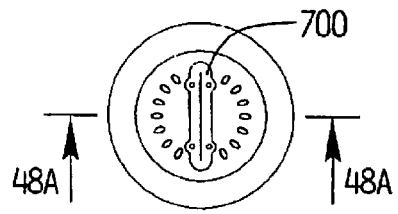
FIG. 49A is a top view of the vascular device and valve of FIG. 48.
Figure 48B:
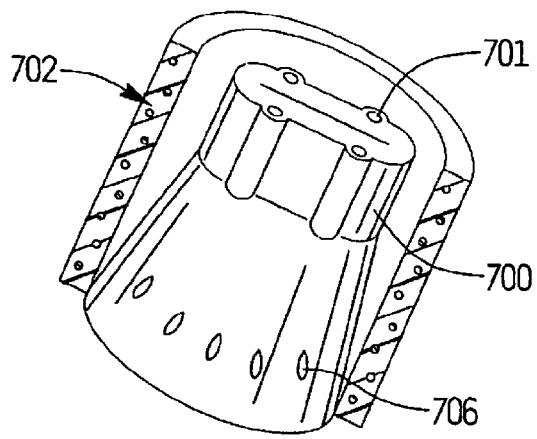
FIG. 48B is a perspective view of the replacement valve of FIG. 48A, with a portion of the covered stent cut away, showing the valve in the closed position.
Figure 49B:
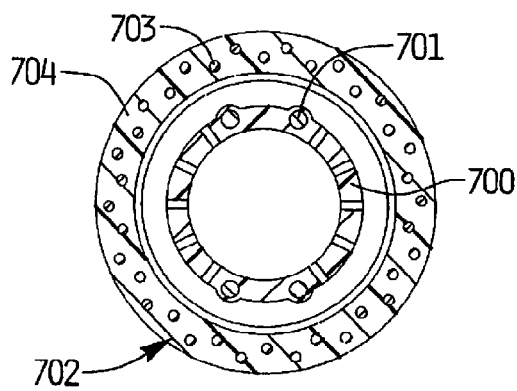
FIG. 49B is a cross-sectional view taking along lines B-B of FIG. 49A.
Figure 48C:
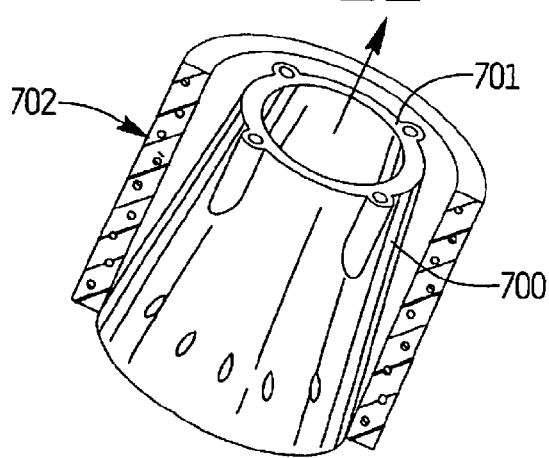
FIG. 48C is a view similar to FIG. 48A except showing the valve in the open position.

In the embodiment of FIGS. 48-49, valve 700 is in the form of a duckbill valve similar to FIGS. 42-44, except the valve is reinforced with metal wires or struts 701. The vascular device is shown in the form of a covered stent 702, with the metal stent 703 embedded in the graft material 704. The valve can include blood drainage slits 706 as shown.

Replacement Valve

The present invention also contemplates in another aspect use of the various valve configurations as replacement valves without the use of a vascular device which brings the walls radially inwardly. The patient's valve can be removed or alternatively left in place and the replacement valve of the present invention placed upstream or downstream of the patient's valve. In such applications, the valve is attached to a support structure, such as a shape memory stent, and is maintained in an open position within the vessel to retain the valve. FIGS. 50 and 51 shown an example of a type of support structure for holding the valve.

More specifically, in the embodiment of FIGS. 50 and 51, instead of a metal framework, the valve 750 is attached to a rolled up cylindrical ring or metal band 752. The ring 752 can be made of shape memory material with its memorized position being an expanded position of FIGS. 50 and 51. The valve 750 is similar to valve 500 of FIG. 38A, except it has a larger reinforcement ring 754, and is cylindrical instead of conical in configuration.

In the embodiment of FIGS. 52-54, the valve 800 has a plurality of drainage holes 802 which function in a similar manner as drainage slits 562 of valve 560 of FIGS. 38-39.

The overlapping cylindrical support member 806 is shown in the contracted delivery position in FIG. 54B and in the expanded position in FIG. 54A. Valve 800 is longitudinally offset with respect to cylindrical member 806.

In the embodiment of FIG. 55, valve 850 is in the form of a duckbill valve and extends from cylindrical support member 856.

It should be appreciated that the valves 850, 800 and 750 can be used with any of the vascular devices described above. Conversely, any of the foregoing valves can be used with cylindrical supports 752, 806. Also, the valves can be attached at the proximal end, distal end, or intermediate the proximal and distal ends of the vascular devices.

The foregoing valves can be attached to the vascular devices, the framework structures and the cylinders, by sewing, molding or other techniques. The valves can be composed of a variety of materials such as PET, PTFE, polycarbonate polyurethane, swine intestinal submucosa, collagen and other biomaterials. The valve and /or the vascular device surface can optionally be coated with anti-platelet or anti-thrombin/anti-clotting materials, 2b/2a coating, receptors, heparin coating, endothelial cell coating, etc.

While the above description contains many specifics, those specifics should not be construed, as limitations on the scope of the disclosure, but merely as exemplifications of preferred embodiments thereof. For example, instead of a balloon to expand the device to its second expanded diameter/condition, a mechanical means such as an expandable wire frame can be utilized. Also, instead of moving the sheath to expose the vascular device, the catheter can be advanced with respect to the sheath or both the catheter and sheath can move relative to each other in opposite directions. Those skilled in the art will envision many other possible variations that are within the scope and spirit of the disclosure as defined by the claims appended hereto.

What is claimed is:

1. A vascular device for treating venous valve insufficiency by an intravascular approach to a target vessel, the device comprising a body and a plurality of vessel penetrating members extending radially from the body in a direction away from a longitudinal axis of the body, the body composed of shape memory material with a low profile insertion position of a first cross-sectional dimension, a shape memorized configuration being of a second reduced cross-sectional dimension but of larger cross-sectional dimension than the first cross sectional dimension and a vessel wall engagement position having a third cross-sectional dimension greater than the second cross-sectional dimension, the vessel engaging members having penetrating tips to penetrate the vessel wall and securely grasp the vessel wall for approximation of the wall, the body movable from the vessel wall engagement position, wherein the penetrating tips of the vessel engaging members penetrate to grasp the vessel wall, toward the shape memorized configuration to thereby bring the vessel wall radially inwardly so the vessel wall is changed from a first diameter to a second diameter, the second diameter being less than the first diameter, such reduction in diameter enabling the treatment of venous valve insufficiency by one of a) bringing the vessel wall to the second diameter such that existing valve leaflets extending radially inwardly from an internal portion of the vessel wall move closer together to thereby reduce a gap in the leaflets to prevent retrograde flow which gap otherwise is insufficient for proper closing of the valve which results in improper functioning of the valves such that retrograde blood flow is not prevented or b) implantation of a replacement valve extending from the vascular device and connected thereto and implanted with the vascular device to prevent retrograde blood flow as the replacement valve moves to a closed position.

2. The device of claim 1, wherein the device is expandable by a balloon positionable within an internal portion of the body.

3. The device of claim 1, wherein the penetrating tips include a hook having a piercing tip to prevent axial movement of the pierced vessel and a barb to restrict radial movement of the pierced vessel.

4. The device of claim 1, wherein the device is laser cut from a tube.

5. The device of claim 1, wherein the vascular device is positionable upstream of the leaflets of the vessel.

6. The device of claim 5, wherein exposure of the vascular device from the delivery member enables the body to expand from a collapsed insertion position.

7. The device of claim 1, wherein the vascular device is positionable downstream of the leaflets of the vessel.

8. The device of claim 7, wherein exposure of the vascular device from a delivery member enables the body to expand from a collapsed insertion position.

9. The device of claim 1, wherein the device includes a replacement valve having a closed position to prevent blood flow and an open position to enable blood flow therethrough, and a plurality of supports extending into the replacement valve which are movable to move the replacement valve between the closed and opened positions.

10. The device of claim 9, wherein the device is expandable by a balloon positionable within an internal portion of the body.

11. The device of claim 9, wherein the penetrating tips include a hook having a piercing tip to prevent axial movement of the pierced vessel and a barb to restrict radial movement of the pierced vessel.

* * * * *